United States Patent
Demirli et al.

(10) Patent No.: US 8,218,862 B2
(45) Date of Patent: Jul. 10, 2012

(54) AUTOMATIC MASK DESIGN AND REGISTRATION AND FEATURE DETECTION FOR COMPUTER-AIDED SKIN ANALYSIS

(75) Inventors: Ramazan Demirli, Whippany, NJ (US); Deepak Kumar Gaddipati, Kokomo, IN (US)

(73) Assignee: Canfield Scientific, Incorporated, Fairfield, NJ (US)

( * ) Notice: Subject to any disclaimer, the term of this patent is extended or adjusted under 35 U.S.C. 154(b) by 833 days.

(21) Appl. No.: 12/362,985

(22) Filed: Jan. 30, 2009

(65) Prior Publication Data

US 2009/0196475 A1    Aug. 6, 2009

Related U.S. Application Data

(60) Provisional application No. 61/025,371, filed on Feb. 1, 2008.

(51) Int. Cl.
*G06K 9/00* (2006.01)
*G06K 9/34* (2006.01)

(52) U.S. Cl. ......... 382/164; 382/162; 382/168; 382/171

(58) Field of Classification Search .................. None
See application file for complete search history.

(56) References Cited

U.S. PATENT DOCUMENTS 6,263,113 B1    7/2001   Abdel-Mottaleb et al.
(Continued)

FOREIGN PATENT DOCUMENTS
FR     2 864 300 A1    6/2005

OTHER PUBLICATIONS

Bookstein et al, "Principal Warps: Thin-Plate Splines and the Decomposition of Deformations", Jun. 1989, pp. 567-585, vol. 11, No. 6, IEEE Transactions on Pattern Analysis and Machine Intelligence.

(Continued)

*Primary Examiner* — Li Liu
(74) *Attorney, Agent, or Firm* — Brosemer, Kolefas & Assoc., LLC

(57) ABSTRACT

Methods and systems for automatically generating a mask delineating a region of interest (ROI) within an image containing skin are disclosed. The image may be of an anatomical area containing skin, such as the face, neck, chest, shoulders, arms or hands, among others, or may be of portions of such areas, such as the cheek, forehead, or nose, among others. The mask that is generated is based on the locations of anatomical features or landmarks in the image, such as the eyes, nose, eyebrows and lips, which can vary from subject to subject and image to image. As such, masks can be adapted to individual subjects and to different images of the same subjects, while delineating anatomically standardized ROIs, thereby facilitating standardized, reproducible skin analysis over multiple subjects and/or over multiple images of each subject. Moreover, the masks can be limited to skin regions that include uniformly illuminated portions of skin while excluding skin regions in shadow or hot-spot areas that would otherwise provide erroneous feature analysis results. Methods and systems are also disclosed for automatically registering a skin mask delineating a skin ROI in a first image captured in one imaging modality (e.g., standard white light, UV light, polarized light, multi-spectral absorption or fluorescence imaging, etc.) onto a second image of the ROI captured in the same or another imaging modality. Such registration can be done using linear as well as non-linear spatial transformation techniques.

20 Claims, 26 Drawing Sheets

U.S. PATENT DOCUMENTS

| | | | |
|---|---|---|---|
| 6,332,033 | B1 | 12/2001 | Qian |
| 6,343,141 | B1 * | 1/2002 | Okada et al. ............... 382/118 |
| 6,526,161 | B1 | 2/2003 | Yan |
| 6,571,003 | B1 | 5/2003 | Hillebrand et al. |
| 6,600,830 | B1 | 7/2003 | Lin et al. |
| 6,633,655 | B1 * | 10/2003 | Hong et al. ............... 382/118 |
| 6,690,822 | B1 | 2/2004 | Chen et al. |
| 6,816,611 | B1 | 11/2004 | Hagiwara et al. |
| 7,039,222 | B2 | 5/2006 | Simon et al. |
| 7,058,209 | B2 | 6/2006 | Chen et al. |
| 7,218,759 | B1 | 5/2007 | Ho et al. |
| 7,233,693 | B2 | 6/2007 | Momma |
| 7,239,726 | B2 | 7/2007 | Li |
| 7,454,046 | B2 | 11/2008 | Chhibber et al. |
| 2004/0028263 | A1 | 2/2004 | Sakamoto |
| 2007/0104472 | A1 * | 5/2007 | Quan et al. ................. 396/79 |
| 2007/0147700 | A1 * | 6/2007 | Jeong et al. ............... 382/266 |
| 2008/0212894 | A1 * | 9/2008 | Demirli et al. ............. 382/276 |

OTHER PUBLICATIONS

F.J. Canny, "A Computational Approach to Edge Detection", Nov. 1986, pp. 679-698, vol. PAMI 8, No. 6, IEEE Transactions on Pattern Analysis and Machine Intelligence.

R.L. Hsu, "Face Detection in Color Imaging", May 2002, pp. 696-706, vol. 24, No. 5, IEEE Transactions on Pattern Analysis and Machine Intelligence.

M. Levin et al, "Nonlinear color space and spatiotemporal MRF for hierarchial segmentation of face features in video", Jan. 2004, pp. 1-9, vol. 13, No. 1, IEEE Transactions in Image Processing.

N. Otsu, "A Threshold Selection Method from Gray-Level Histograms", Jan. 1979, pp. 62-66, vol. SMC-9, No. 1, IEEE Transactions on Systems, Man and Cybernetics.

S.L. Phung et al, "Skin Segmentation Using Color Pixel Classification: Analysis and Comparison", Jan. 2005, pp. 148-154, vol. 27, No. 1, IEEE Transactions on Pattern Analysis and Machine Intelligence.

C. Xu and J.L. Prince, "Snakes, Shapes and Gradient Vector Flows", Mar. 1998, pp. 359-369, IEEE Transactions on Image Processing.

Q. Hu et al, "Supervised Range-Constrained Thresholding", Jan. 2006, pp. 228-240, vol. 15, No. 1, IEEE Transactions in Image Processing.

G.N. Stamatas et al, "Non-Invasive Measurements of Skin Pigmentation in Situ", Sep. 2004, pp. 618-626, vol. 17, Pigment Cell Research.

Brochure for Visia Complexion Analysis System for Facial Skin Analysis, Canfield Scientific, Feb. 2007.

Brunelli and T. Poggio, "Face Recognition: Feature versus Templates", Oct. 1993, pp. 1042-1052, vol. 15, No. 10, IEEE Transactions on Pattern Analysis and Machine Intelligence.

Kass et al, "Snakes: Active Contour Models", 1998, pp. 321-331, International Journal of Computer Vision.

K.M. Lam and H. Yan, "An Improved Method for Locating and Extracting the Eye in Human Face Images", Aug. 1996, pp. 25-29, vol. 3, Proceedings of the 13th International Conference on Pattern Recognition.

Reddy et al, "An FFT based technique for translation, rotation and scale invariant image registration", Aug. 1996, pp. 1266-1271, vol. 5, No. 8, IEEE Transactions on Image Processing.

Yilmaz and M. Shah, Automatic Feature Detection and Pose Recovery of Faces, Jan. 2002, pp. 23-35, The 5th Asian Conference on Computer Vision.

K. Sobottka et al., "Segmentation and tracking of faces in color images," Auto. Face and Gesture Recognition 1996, Proceedings, IEEE, Oct. 14, 1996.

Saber et al., "Frontal-view face detection and facial feature extraction using color, shape and symmetry based cost functions," Pattern Recognition Letters, Elsevier, vol. 19, No. 8, Jun. 1, 1998.

M.C. Shin et al, "Does colorspace transformation make any difference on skin detection?," Appl. of Comp. Vision 2002, Proceedings, IEEE, Dec. 3, 2002.

D.A. Forsyth et al., "Identifying nude pictures," Appl. of Comp. Vision 1996, Proceedings, IEEE, Dec. 2, 1996, pp. 103-108.

* cited by examiner

Nostrils Row

AUTOMATIC MASK DESIGN AND REGISTRATION AND FEATURE DETECTION FOR COMPUTER-AIDED SKIN ANALYSIS

RELATED PATENT APPLICATION

The present application claims priority from U.S. Provisional Patent Application No. 61/025,371, filed on Feb. 1, 2008, which is incorporated herein by reference in its entirety.

FIELD OF THE INVENTION

The present invention relates to computer-aided skin analysis, and more particularly to the automatic design and registration of masks delineating regions of interest in images of skin.

BACKGROUND INFORMATION

Computer-aided skin analysis has become widespread in the past decade with the availability of controlled lighting systems and sophisticated digital-image capture and processing capabilities. The skin analysis is typically limited to a particular area or region of interest (ROI) within a larger anatomical area by applying a mask thereto to delineate the ROI. The analysis often involves processing the ROI to identify and/or diagnose skin features, abnormalities or conditions such as skin color, hyperpigmented spots, wrinkles, skin texture, acne, rosacea, hyperpigmentation, and wrinkling, among others.

Because of the great emphasis placed on the appearance of the face, much computer-aided skin analysis work has focused on facial skin. There are a number of commercially available systems for facial skin imaging that can capture digital images in a controlled manner. These systems are often coupled to computer analysis systems for the visualization and quantification of visible skin features in standard white light images such as hyperpigmented spots, wrinkles, and texture, as well as non-visible features in hyperspectral absorption or fluorescence images such as UV spots and UV porphyrins. There are also a number of more sophisticated skin imaging systems such as the VISIA-CR imaging system, available from Canfield Scientific, Inc., that can provide multispectral images for the analysis of more complex skin conditions, such as acne.

Some limited work has been done in the design of skin masks for the delineation of skin ROIs to be analyzed. U.S. Pat. No. 6,571,003 to Hillebrand, et al., entitled "Skin imaging and analysis systems and methods," describes a method of performing skin analysis within an operator designed ROI, i.e., a manually-designed polygon mask defining a skin patch created with the use of a computer. Guidelines for designing a skin mask for oblique-view face images by using some facial feature points as reference points are also described. The methods described therein, however, involve focused user interaction and are prone to user errors and inconsistencies in the masks designed by different users as well as masks designed by the same user.

U.S. Pat. No. 7,454,046, Chhibber, et al., entitled "Method and system for analyzing skin conditions using digital images," describes a method to generate a skin map for computer analysis of visible skin features on a face image captured from a front-viewing angle. A crude mask is obtained by applying fixed thresholds to the R, G, and B channels of the color image. This mask is reduced by eliminating some of the non-skin pixels using a second threshold in one of the color spaces and further modified by a fixed size template mask. This method is prone to intensity changes in the image. As a result it may not be reproducible for follow-up visits and does not account for different skin types. Furthermore, this method does not provide a continuous map with well defined borders.

U.S. Pat. No. 7,233,693, Momma, et al., entitled "Methods and systems for computer analysis of skin image" describes a skin analysis system and method in which fixed shape circular masks—for front-view face images—are placed automatically on a subject's cheeks and a rectangular shape mask is placed on the subject's forehead and further adjusted by the user. These types of masks cover only a portion of the available skin in the region of interest such as the face, cheek and forehead, and are not well-fitted to the natural shape of the face.

U.S. Patent Application US2004/0028263 A1, Sakamato, et al., entitled "Digital zoom skin diagnostic apparatus," describes a facial skin imaging and analysis system in which several fixed-size, small square patches (200×200 pixels) are manually placed on desired locations of the face. These patches cover only a small portion of the facial skin. As a result, computer analysis performed on these patches does not necessarily represent the skin conditions of the entire face.

Most other computer-aided skin analysis for clinical research studies utilizes manually designed skin masks based on a set of guidelines. However, the system operators interpret these guidelines subjectively. As a result, a high degree of variation arises in the mask design from one user to another. This manual process can also be tedious depending on the complexity of the ROI.

Moreover, in most clinical research studies, skin analysis algorithms are often performed on a collection of images in a batch mode. Prior to the analysis, a mask for each image needs to be designed manually for the desired skin ROI. The manual masking process for many images is time-consuming and once again prone to user errors. The errors and inconsistencies introduced by the user(s) in the mask design will have a negative impact on the overall analysis results, such as for example, on the comparability of analysis across different subjects or across different sessions for the same subject.

Image capture systems for computer-aided skin diagnoses often capture a number of images in several different imaging modalities such as standard white light, UV light with filters, blue-light, cross-polarized light, etc. Even though the images are usually captured in sequence with a minimal time delay, there is often a noticeable misalignment among these images because of the difficulty in keeping the subject perfectly still during the image capture process. This misalignment makes the mask designed for a skin site in one imaging modality not directly usable for the image of the same skin site captured in another imaging modality. The mask needs to be registered properly for the second image for meaningful comparison purposes. The registration of the mask can be performed manually, but this process is even more difficult than registering the masks in the same imaging modality because the visual comparison of images in different modalities is difficult for the human eye.

For most computer-aided skin analysis applications it is essential to use a mask designed for a baseline image of the skin site for a subsequent image of the same skin site captured in the same or another imaging modality. For quantitative comparison of skin analysis results, the ROI should cover the same areas for the two images of the same skin site. As mentioned, most often there is a misalignment between the images of the same skin site captured at different time points due to a change in the pose or expression of the subject. Consequently, for quantitative analysis purposes, a mask designed for the first captured image could not be directly usable for the second captured image. Even with controlled image capture systems, there can be significant misalignment in images of the same skin site captured at different points in time.

Some image processing systems offer some manual correction capability by allowing a user to visually inspect the mask overlaid on the first image and the same mask overlaid on the second image, and to adjust the mask. This manual correction process is time-consuming and prone to user errors. The misalignment issue also arises between images of a skin site captured with different imaging modalities.

Therefore, in view of the foregoing considerations, it is highly desirable to automate and standardize the process of designing the ROI or skin mask. Such an automated and standardized process can provide more meaningful and consistent skin analysis, eliminate user errors, and speed up the creation of the mask. Furthermore, it is highly desirable to use an ROI designed for an image of the skin site captured in one imaging session or imaging modality for another image of the same skin site captured in a subsequent session or another imaging modality.

SUMMARY OF THE INVENTION

In several exemplary embodiments, the present invention provides methods and systems for automatically generating a mask delineating a region of interest (ROI) within an image containing skin. The image may be of an anatomical area containing skin, such as the face, neck, chest, shoulders, arms or hands, among others, or may be of portions of such areas, such as the cheek, forehead, or nose, among others. The mask that is generated is based on the locations of anatomical features in the image, such as the eyes, nose, eyebrows and lips, which can vary from subject to subject and image to image. As such, a mask generated in accordance with the present invention can be adapted to individual subjects and to different images of the same subject, while delineating an anatomically standardized ROI. This allows for standardized, reproducible skin analysis over multiple subjects and/or over multiple images of each subject.

The present invention provides methods and systems that facilitate quantitative computer-aided analysis of skin, including automatic skin mask design methods and systems for a specific skin site based upon an image of the skin site and a skin mask template associated with the skin site. The present invention also provides automatic skin mask design methods and systems for full-face images, captured in oblique- or frontal-view, in which the resultant skin mask is based upon the locations of facial landmark points extracted from the related full-face image.

The present invention also provides methods and systems to process the image of a skin site to obtain skin regions useful for skin analysis. These skin regions include uniformly lighted portions of skin and exclude skin regions in shadow or hot-spot areas that would otherwise provide erroneous feature analysis results.

The present invention further provides methods and systems to refine a skin map displaying the skin regions of a skin site according to user-defined boundaries or guidelines for that skin site. The generation of an initial skin mask contour based on the refined skin map is disclosed as is the application of a contour optimization process to the initial skin mask contour to generate a final skin mask contour.

The present invention provides methods and systems to design skin masks using facial landmark points. The use of facial landmark points to divide skin masks into sub-regions of interest is also disclosed.

The present invention further provides methods and systems to detect facial landmark points for front- or oblique-view full-face images based upon representative templates for the regions associated with the landmark points.

The present invention provides methods and systems for automatically registering a skin mask delineating a skin ROI in a first image captured in one imaging modality (e.g., standard white light, UV light, polarized light, multi-spectral absorption or fluorescence imaging, etc.) onto a second image of the ROI captured in the same or another imaging modality. The masked portions of the first and second images may be used for a variety of purposes, for example, comparison of skin features in different lighting modalities, side-by-side visual examination, skin analysis comparison before and after treatment, etc.

The registration methods and systems of the present invention can be applied to skin masks regardless of how they were generated, including manually designed masks and masks that have been generated automatically, such as in accordance with the aforementioned embodiments of the present invention.

An embodiment of the present invention addresses the problem of shape-preserving skin mask registration. Methods and systems are disclosed to register a skin mask designed for a particular image of a skin site for another image of the same skin site by estimating a linear spatial transformation between the images of the same skin site. Registration methods and systems are also disclosed which use a non-linear spatial transformation between the images of the same skin site.

The present invention offers several features and advantages useful for computer-aided skin analysis. First, a mask generated in accordance with the present invention has a standard shape for a particular skin site (e.g., face, cheek, forehead, chest, etc.) Moreover, the mask generation of the present invention is adaptive to a given skin site, such as the face, and adjusts to the shape of a given subject's skin region such as the face, cheek, forehead, etc.

Additionally, a mask generated in accordance with the present invention can be limited to cover only uniformly lit portions of skin, avoiding skin regions not useful or amenable to computer analysis such as regions degraded by shadow or reflection. Skin covered by hair and non-skin body parts can also be avoided. Skin ROIs can thus provided that are useful for a variety of applications, including computer analysis and diagnosis of skin, visualization of skin conditions and appearance, and skin color/texture animations and simulations, among others.

Additionally, a skin mask can be designed in accordance with the present invention to cover the maximum available skin area for a given skin site image; it defines a piecewise continuous region clearly bounded by a smooth closed curve; it has a fluid and esthetic shape, hence is easy to visualize and interpret by the users; and the mask design is consistent across skin types and colors.

The automatic skin mask design methods and systems disclosed herein can be utilized in or with a variety of skin image capture and analysis methods and systems.

The above and other aspects and features of the present invention will be apparent from the drawings and detailed description which follow.

DETAILED DESCRIPTION

Figure 1:
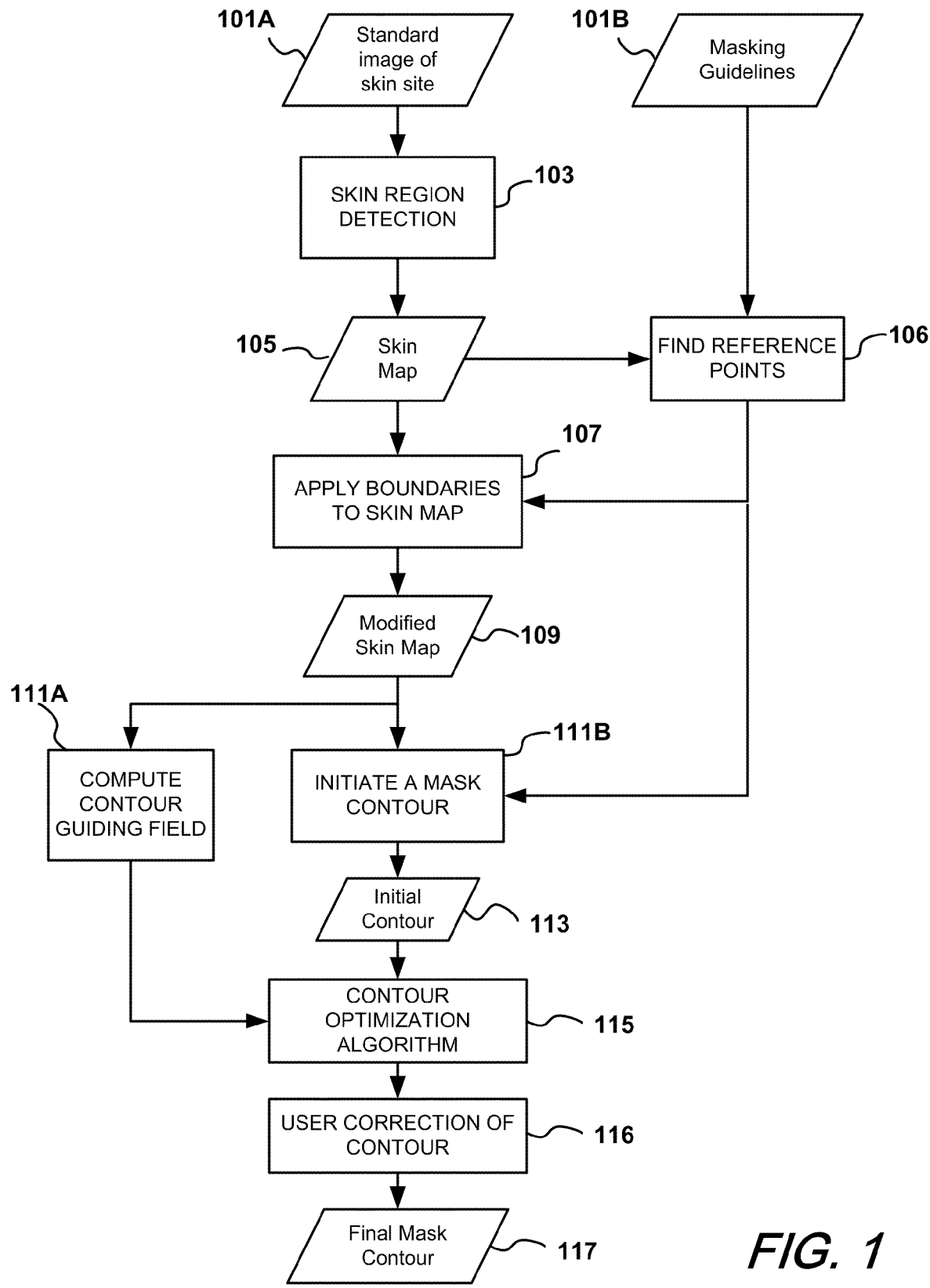
FIG. 1 is a high-level flowchart of an exemplary method for generating a skin mask from the image of a known skin site and a desired generic skin mask template associated with that skin site, in accordance with the present invention.

FIG. 1 is a high-level flowchart illustrating an exemplary embodiment of a method of generating a mask for an image of a skin site in accordance with the present invention. The method takes as an input a close-up image 101A of a known skin site (e.g., cheek, forehead, chest etc.) preferably captured under standardized and reproducible illumination and pose conditions. In order to provide standardized and reproducible illumination conditions, the image 101A is preferably captured with an automated and controlled skin image capture system, such as the VISIA Complexion Analysis System for facial skin analysis (hereafter referred to as VISIA) available from Canfield Scientific, Inc. For skin images involving other body parts, either an open-field or closed-field image capture system can be used in which a camera is placed in a fixed position and orientation relative to the subject while the subject is positioned in a standard manner. FIG. 2A shows an illustrative skin site image captured with the VISIA system focusing on the cheek area of the face of a subject.

In the exemplary embodiment of FIG. 1, the skin site image 101A captured with standard light can be expressed as an RGB (red, green, blue) color image. However, the skin site image can also be captured in a different lighting modality, or with a multi-spectral imaging system, provided that skin regions can be discriminated based upon a skin-index measure (e.g., melanin and/or hemoglobin concentrations) derived from the image captured.

Figure 2B:
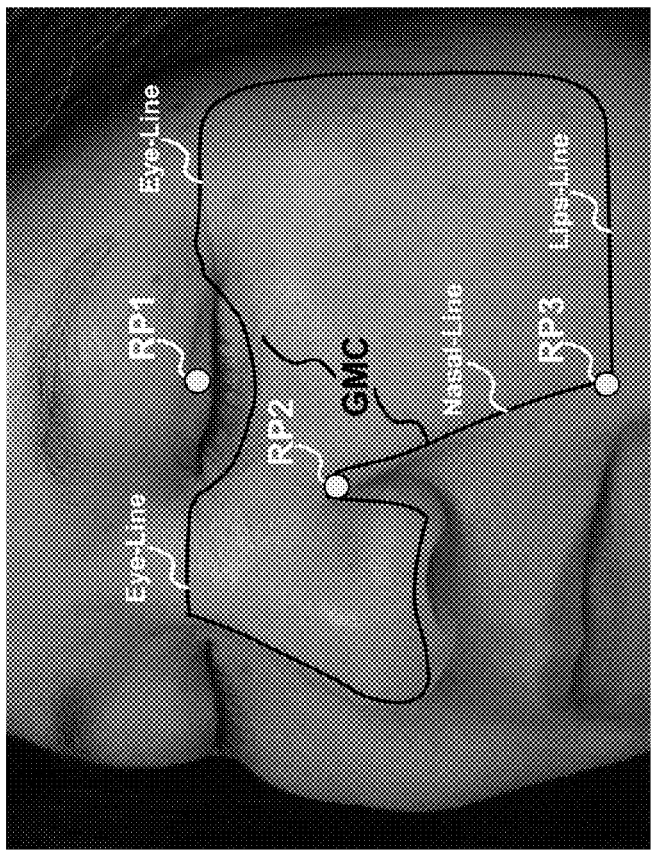
FIGS. 2B through 2E show various illustrative intermediate images relating to the exemplary method of FIG. 1.
Figure 2A:
FIG. 2A shows an illustrative facial image for which a mask is to be designed in accordance with the exemplary method of FIG. 1.

In FIG. 2B, a typical skin mask of the cheek region of the face is shown enclosed by the contour GMC. The skin mask of FIG. 2B is illustrative of a skin mask that may be generated by the method of FIG. 1. The particular skin mask shown is intended to cover skin regions below the eye level down to the regions around the lips level including the nose area but excluding the regions under the nasolabial fold line, and all the available skin regions towards the end of the cheek. Note that some segments of the mask contour GMC follow natural boundaries or features of the skin whereas other segments do not. Contour segments of the former type include, for example, the curve of the nose, the curve of the bottom of the eye, and the right-most line marking the end of the cheek region. Contour segments of the latter type include, for example, the eye-lines, nasal-line, and lips-line. The contour segments that do not follow natural skin boundaries or features can be defined or selected, for example, in accordance with user input so as to yield a mask that covers a desired skin region-of-interest (ROI).

A set of skin masking guidelines 101B associated with the captured skin site image 101A is used to guide the skin mask design process to generate a skin mask that covers the desired skin ROI. The guidelines 101B may specify, for example, that the skin ROI is between the eye-lines and the lips-line, in the case of a cheek-region mask, such as that of FIG. 2B. The guidelines may be specified by a user, for example, using a graphical user interface, or any other suitable means.

At 103, the skin regions of the captured skin site image 101A are segmented using a skin region detection procedure. There are several skin detection/segmentation methods available that have been developed for a variety of purposes. The purpose of the skin region detection procedure at 103 is to segment out useful portions of skin regions for computer-aided skin analysis. One skilled in the art can appreciate the challenge of analyzing skin regions with shadows, excessive shine, and hair color that is close to skin color. An exemplary skin detection process will be described below in greater detail.

Figure 2D:
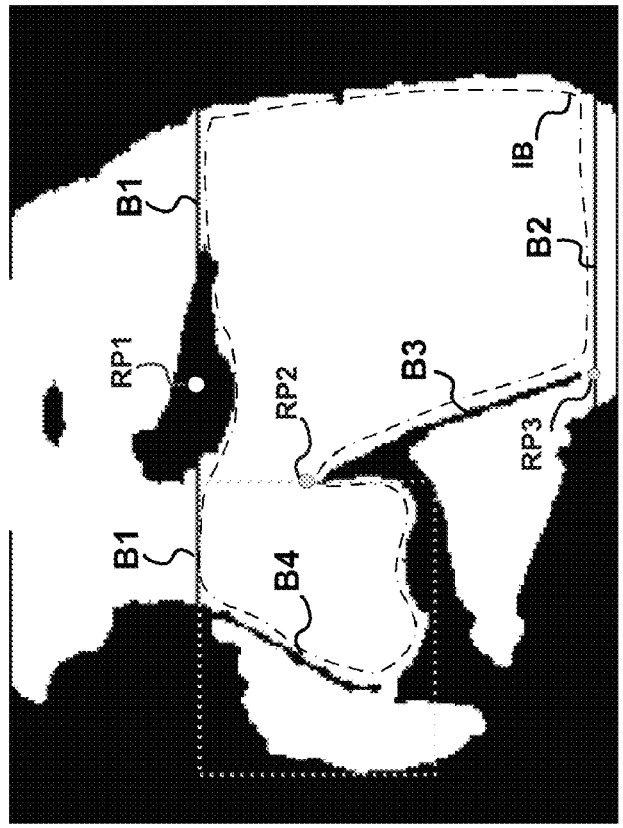
Figure 2C:

The procedure 103 returns a skin map 105 in which useful skin areas are displayed as white and other areas, such as non-useful skin areas and non-skin areas, are displayed as black. An image of an exemplary skin map 105 is shown in FIG. 2C based upon the captured skin site image 101A in FIG.

2A. The skin map 105 contains skin regions useful for analysis while excluding non-skin regions (e.g., lips, nostrils, eyes, hair, and background) and skin regions that receive relatively less light (e.g., dark skin areas behind the nose profile, the neck region, shadows under the eyes and in the nasal folds, mouth folds, etc.) The skin map 105 defines a framework in which the final mask will be designed.

At 106, a set of reference points are located in the skin map 105 based on the guidelines 101B. For the illustrative oblique-view image of FIG. 2B and the guidelines discussed above, three reference points RP1, RP2 and RP3 are shown. RP1 marks the center of the eye, RP2 marks the top-end of the nasolabial line, and RP3 marks a point at some horizontal distance from the corner of the lips. This distance is selected to locate RP3 generally along the lips line and near the vicinity of the nasal line. For a 220 PPI skin-map image, a distance of approximately 10 pixels can be used, or a distance can be determined based on a population average, for example. Thus, for example, if the guidelines 101B call for a mask that is to be limited to the region below the eye line, above the lips line, and outwards of the nasal line (as shown in FIG. 2B), then the reference points RP1-RP3 will be determined. For a different set of guidelines, a different set of reference points may be determined.

The reference points (RP1-RP3) can be determined at 106 in a variety of ways in accordance with several different embodiments. In one embodiment, the user can specify these points via a graphical user interface, for example, such as with mouse clicks on an image such as the one shown in FIG. 2B. In another embodiment, these points are determined automatically using landmark detection algorithms, for example, facial feature detection algorithms. Methods to detect some key facial landmark points are presented below. In a preferred embodiment, these reference points are detected directly from the skin map 105, such as that shown in FIG. 2C. The skin map shown discriminates the eye area, the lips and mouth area, and the nasolabial-fold line since these regions will be treated as non-skin. The center of the eye RP1 can be found by scanning the skin map 105 for the eye-hole starting from the top. RP2 can be found as the coordinates of the first dark pixel below the eye region. Similarly, the corner of the lips RP3 can be found by scanning the skin map 105 from the bottom up, by looking, for example, for the greatest change in the number of white pixels per row.

Operation then proceeds to 107 in which boundaries are applied onto the skin map 105. A first set of boundaries applied at 107 are based upon the reference points (e.g., RP1-RP3) found in 106. These boundaries can be thought of as "user-defined" in the sense that they are based on the reference points (from 106) which are determined in accordance with the user-specified masking guidelines 101B. An illustrative set of user-defined boundaries is shown in FIG. 2D as lines B1-B3 drawn on the skin map shown in FIG. 2C. The upper line B1 drawn through the dark region representing the eye area intersects the reference point RP1 at the center of the eye and serves to limit the final skin mask to an area below the eye-lines, as specified by the illustrative guidelines (101B). The lower line B2 drawn through the lips and mouth region intersects the reference point RP3 and serves to limit the final skin mask to an area above the lips-line. The diagonal line B3 starting from the nasal fold near the nose (RP2) and ending at the corner of the lips and mouth (RP3) is drawn to exclude skin regions under the nasolabial line.

A second set of boundaries applied at 107 are based on the natural boundaries of skin. For example, the curved outline of the ridge of the nose, shown in FIG. 2D as boundary B4, is one such boundary. Note, however, that although this boundary may not always be visible in the skin map (see FIG. 2C), it can be recovered using an edge detection algorithm in a rectangular area covering the nose. For example, Canny's edge detector, whose filter size is adjusted for the thickness of the nose edge can be used for this purpose. (See F. J. Canny, "A computational approach to edge detection", IEEE Transactions on Pattern Analysis and Machine Intelligence, Vol. 8, No. 6, pp. 679-698, 1986.) The rectangular area covering the nose can be determined based upon the reference point RP2 and the starting point of the line B1. As shown in FIG. 2D with dotted lines, the rectangle includes the aforementioned points and extends left to the starting column of the skin map and down a predetermined amount based on the expected length of the nose (based for example on population measurements).

As described below, additional boundaries can be defined to divide the final skin mask into sub-regions based upon the provided reference points, or another set of reference points that can be deduced from the skin map, or the original skin image itself.

The above-described boundaries (B1-B4) are applied to the skin map 105 (e.g., FIG. 2C) to derive a modified skin map 109 (e.g., FIG. 2D). The modified skin map 109 provides a frame within which the final mask is to be generated.

One can visualize the intended mask by combining natural and user-defined boundaries. In FIG. 2D, an innermost boundaries contour IB is shown. IB can be perceived by a human observer as the contour encapsulating the desired skin mask based on available skin areas and masking guidelines. In an ideal case, such a contour can be traced with a contour-tracing algorithm in which the contour is continuous, smooth, and follows the true boundaries of the desired region. Most often, however, this contour will have branches and gaps which would make it difficult for the contour-tracing algorithm to find the true boundaries. For example, as seen in FIG. 2D, the edges following the nose profile do not entirely recover the nose profile. The contour is branching if one follows through the eye centerline to the edge of the nose. In addition, there is a gap in the contour around the corner of the lips, which will cause the contour-tracing algorithm to pause.

It is often challenging to segment out objects with low-level image processing techniques such as edge detection or segmentation using histogram thresholding. Most often the boundaries of objects are not clearly visible in images due to non-uniform lighting and imperfect measurements. Low-level image processing methods can only partially recover boundaries of objects while introducing spurious boundaries due to noise and other artifacts in the image.

To address the aforementioned challenges, an embodiment of the present invention incorporates a higher-level knowledge into the mask design through active contour modeling and optimization. Assuming that the object of interest (i.e., the ROI to be delineated by the final mask) is a single object with smooth boundaries, the boundaries can be represented with a closed contour. The problem then becomes estimating the boundaries of such an object with a closed contour based on the provided image. Active contour modeling provides a technique for solving such a boundary-finding problem. Active contour modeling is described in Kass, et al., in "Snakes: Active Contour Models", International Journal of Computer Vision, 1 (4), 321-331, 1988, (hereinafter referred to as the Kass reference).

Figure 2E:
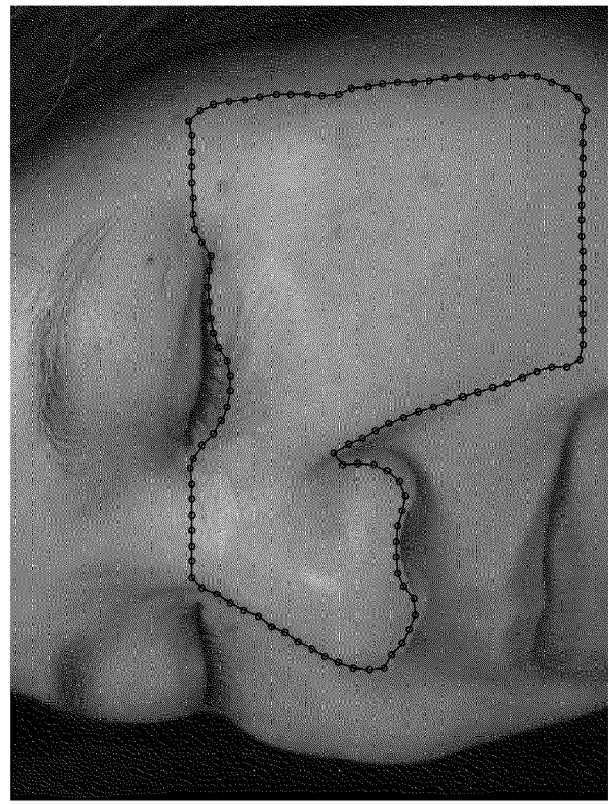

At 111B, an initial contour 113 is automatically generated based on the modified skin map 109. The initial contour 113 is preferably placed in close proximity to the boundaries of the modified skin mask 109 so that an active contour optimization algorithm can converge to a good solution that is preferably global. As shown in FIG. 2E, an exemplary initial contour is drawn on the modified skin map as a polygon IC. The vertices (V1-V7) of the polygon IC are determined based upon a set of critical points, CP1-CP7 in the illustration of FIG. 2E. The point V1 is at the center point between CP1 and CP7. The point V3 is at the center point between CP2 and CP3. The column coordinate of V2 is the mid-column between CP1 and CP2, and its row coordinate is the mid-row between the eye-line and the row of CP4. The point V4 is at a certain diagonal margin (e.g., 10 pixels for 220 PPI image) inland from the point CP6, point V5 is at a certain diagonal margin inland from point CP6, and point V6 is at a certain vertical margin (e.g., 10 pixels) up from point CP4. Point V7 is at a certain diagonal margin away from the intersection point between the horizontal line of CP4 and the vertical line of CP7 towards the bottom-left corner of the image.

The critical points (CP1-CP7) are determined based upon the skin map 105, the reference points (RP1-RP3) and the intersections of the user-defined boundaries (B1-B3) with the skin map. CP1 and CP2 mark the corners of the eye-hole along the eye-line. CP3 is the last skin pixel along the eye-line when scanned from CP2 to the right. CP5 and CP6 are the first and last skin pixels along the lips-line. CP4 is the top of the nasolabial fold and CP7 is the first skin pixel along the eye-line starting from the left. Although seven critical points are shown in the illustrative image of FIG. 2E, the number of critical points determined may vary depending on the skin map. Note that the set of critical points described is for an oblique-view face image and serves as an exemplary set out of many possible sets. Furthermore, the initial contour is also exemplary. One can design any initial contour as long as the contour is in close proximity to the skin-map boundaries.

In a further exemplary embodiment, the initial contour 113 can be edited or input by a user using a graphical user interface, or the like.

At 111A, a process computes a contour-guiding potential field based upon the modified skin map 109. As described below, the contour-guiding potential field is used to drive the initial contour IC to the boundaries of the modified skin map 109. Such a field can be generated using a number of different techniques. Distance transform is one technique for generating an attraction field in close proximity to an object. Gradient vector flow (GVF) is a more sophisticated and iterative technique that computes a smooth and a larger attraction field from the edge information. This technique is described in the reference, C. Xu and J. L. Prince, "Snakes, Shapes, and Gradient Vector Flow," IEEE Transactions on Image Processing, 7(3), pp. 359-369, March 1998, (hereinafter referred to as the Prince reference).

At 115, a contour optimization algorithm takes the initial contour 113 and drives the contour to the boundaries of the modified skin map 109 by optimizing an energy functional based upon the contour-guiding potential field computed at 111A, regularity terms for the smoothness and integrity of the contour, and/or properties of the region (e.g., uniformity) within the contour. The contour-guiding potential field attracts the contour to the boundaries of the modified skin map 109 while the smoothness term ensures that the contour is smooth and the contour integrity term ensures resistance to bending and breaking apart. In a preferred embodiment, a contour optimization algorithm such as described in the Prince reference is used. There are alternative ways to define the energy functional, for example, by using additional terms regarding the properties of the contour, or properties of the region within the contour. For example, one can incorporate a region smoothness term in the energy functional so that the contour is optimized to cover the smooth regions in addition to the other criteria mentioned above. Such a technique is useful for skin mask design since skin regions are expected to be smooth compared to other regions.

The contour optimization algorithm is typically carried out iteratively. The intermediate contours in progressing to the boundaries of the desired skin region can be displayed to provide a visual effect of how the contour automatically snaps to the boundaries.

Figure 2F:
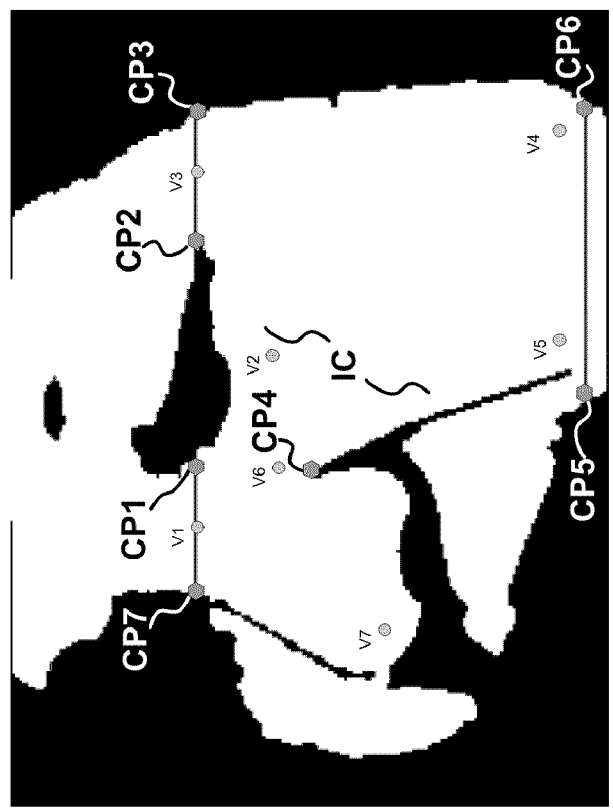
FIG. 2F shows an exemplary skin mask designed in accordance with the method of FIG. 1 overlaid on the original image of FIG. 2A.

The optimized mask contour can be displayed on the original image, such as illustrated in FIG. 2F. Preferably, at 116, the system allows the user to correct any portion of the mask contour, if need be, by giving the user the ability to manipulate points along the contour with a suitable graphical user interface, or the like. For example, by manipulating individual points on the contour, a user can correct a part of the contour that may have leaked over a non-skin area, or a part of the contour that may not be smooth enough, or the user can enlarge the contour to cover a larger portion of available skin regions, among other possibilities. Such optional editing yields the final mask contour 117. The coordinates of the final mask points can then be stored and/or associated with the original image in a database, computer memory, or the like, for later retrieval.

Detection of Skin Regions

As described above with reference to FIG. 1, skin region detection is carried out at 103. An exemplary skin region detection process will now be described in greater detail.

Several skin detection algorithms have been developed for a variety of purposes, including face detection. (For example, see R. L. Hsu, et al., "Face detection in color images", IEEE Transactions on Pattern Analysis and Machine Intelligence, Vol. 24, No. 5, pp. 696-707, May 2002.) If such skin detection algorithms provide an adequate level of granularity, they may be used for skin region detection in accordance with the present invention.

In a preferred embodiment of the present invention, a novel skin detection process is used. An aim of this process is to segment out only the uniformly lit portions of a skin site image if the image contains shadows due to the three-dimensional topology of the skin site or due to a non-uniform light field. For example, if the given skin site image is a face image captured from an oblique or front viewing angle, the process would exclude non-skin regions (eyes, eyebrows, hair, mustache, beard, etc.) as well as shadowy skin regions such as the neck area.

The exemplary skin detection process uses the Individual Typology Angle (ITA) measure, which is used as an indicator of skin. The ITA is computed using the L* and b* channels of the CIE L*a*b* (hereinafter called L*a*b) transformed skin image. (For a detailed description of this metric, see G. N. Stamatas, et al., "Non-Invasive Measurements of Skin Pigmentation In Situ," Pigment Cell Research, Vol. 17, pp: 618-626, 2004.) The ITA is defined for each image pixel (i,j) as $\arctan((L^*[i,j]-50)/b^*[i,j])$ and is related to the melanin concentration of skin. The hypothesis is that the ITA values for skin pixels will be clustered around a value, whereas the ITA values for non-skin pixels are markedly away from the ITA value of skin pixels.

Figure 3:
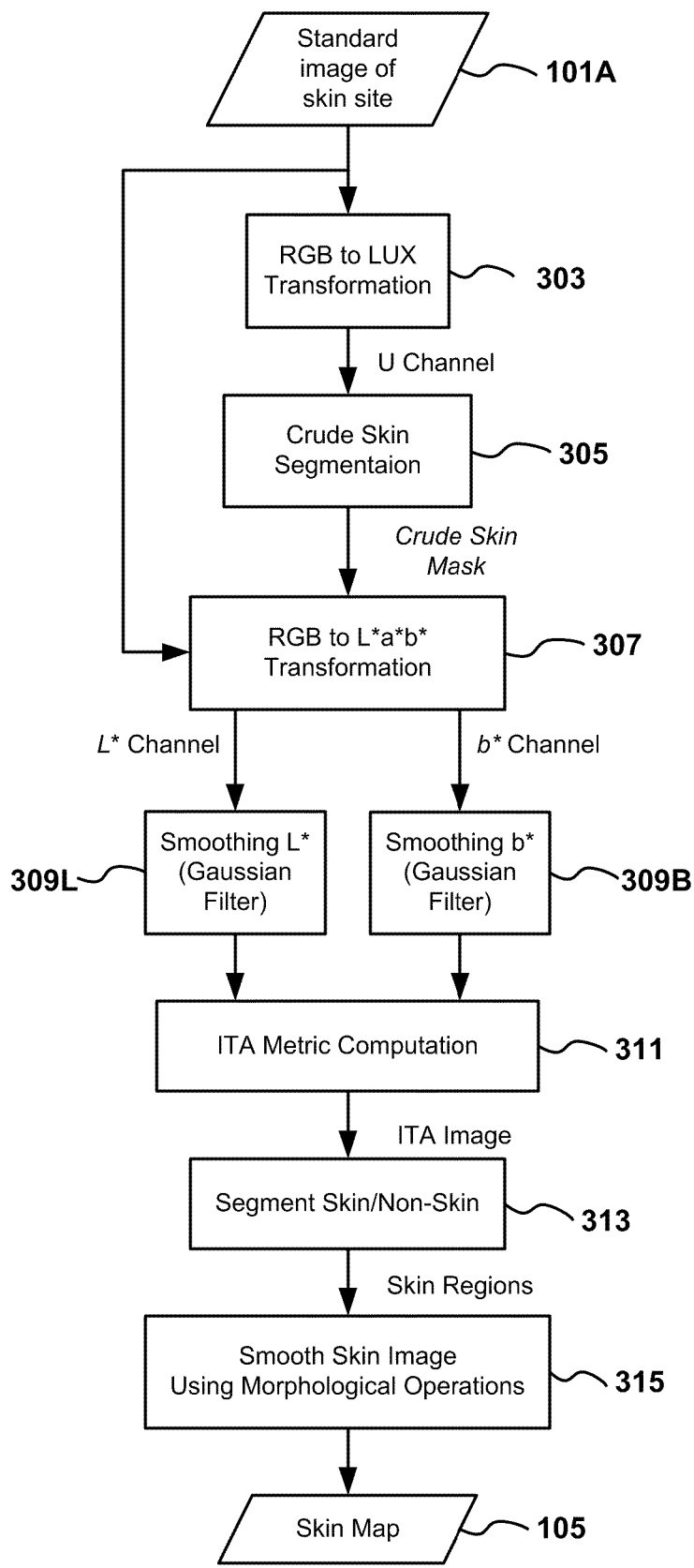
FIG. 3 is a flowchart of a preferred method for segmenting skin regions of a skin site image captured in standard light useful for computer analysis, in accordance with the present invention.

FIG. 3 is a flowchart illustrating an exemplary skin region detection process, in accordance with the present invention, which employs the aforementioned ITA metric. A crude skin detection is performed first to segment out the regions that are clearly not skin from the overall image. For example, for a head image with background, a crude skin map contains the face, partial regions of hair, neck, and eyes. The crude skin detection applied to the image should detect all skin regions of the face but may also include some facial features (eyes, eyebrows, nostrils, lips, hair, etc.) For this purpose, the LUX color space is utilized to segment out the crude skin regions from the close-up image. (See M. Levin, et al., "Nonlinear color space and spatiotemporal MRF for hierarchical segmentation of face features in video," IEEE Transactions in Image Processing, Vol. 13, No. 1, January 2004, hereinafter called the Levin reference.)

As shown in FIG. 3, the process begins with a standard, RGB skin site image (referred to as 101A in FIG. 1) including the background, such as shown in FIG. 2A. At 303, the image is transformed from RGB to LUX space using a technique described in the Levin reference.

At 305, the crude skin regions are segmented out. This can be done, for example, by applying the Otsu thresholding method on the U channel of the LUX image. (See N. Otsu, "A Threshold Selection Method from Gray-Level Histograms," IEEE Transactions on Systems, Man, and Cybernetics, Vol. 9, No. 1, pp. 62-66, 1979, hereinafter, the Otsu reference.) Furthermore, a priori information regarding the ratio of skin regions with respect to the overall skin site image can be incorporated in this thresholding method. (See Q. Hu, et al., "Supervised range-constrained thresholding," IEEE Transactions in Image Processing, Vol. 15, No. 1, pp. 228-240, January 2006, hereinafter the Hu reference.) Alternatively, the segmentation at 305 can be carried out with a thresholding method that uses a fixed threshold for a particular skin type to separate skin and non-skin regions where the fixed-threshold is determined, for example, based on skin data for the general or selected categories of population.

A crude skin mask is generated at 305 which delineates all possible skin regions including the skin regions in shadow. The crude skin mask may also include non-skin regions. The primary goal of the crude skin detection is to eliminate background and other non-body parts. The rest of the skin detection process can then be performed only on the crude mask region, thereby reducing the search space and computational cost.

At 307, the original RGB image masked in accordance with the segmentation performed at 305 is transformed into the L*a*b* space. As such, the subsequent ITA metric computation is performed within the crude skin mask region to further segment out non-skin portions of the skin site. Because the division and inverse tangent operations of the ITA metric computation are sensitive to noise, it is preferable to first smooth the L* and b* channels. As shown, such smoothing can be done at 309L and 309B, respectively, by filtering the L* and b* channel images with 2D Gaussian filters or other similar techniques. In an exemplary embodiment, the variances of such filters are chosen as 5 for the L* channel and 1.5 for the b* channel for an image resolution of 220 pixels per inch (PPI).

At 311, the ITA is computed for each pixel (i,j) within the crude mask region in accordance with the expression arctan $((L^*[i,j]-50)/b^*[i,j])$. The ITA image is a gray image in the range of [0-90], with smaller values of ITA corresponding to skin pixels and larger values corresponding to non-skin pixels. The ITA image is segmented at 313 into two classes of regions using, for example, Otsu Thresholding. For this purpose, a histogram of the ITA image is computed only in the crude mask region. Based on the histogram, the Otsu Thresholding method returns a threshold that will segment this image into two classes with minimum inter-class variance. Furthermore, a priori information regarding the ratio of skin regions with respect to the overall skin site image can be incorporated in this thresholding method. (See the Hu reference.) For example, for a typical oblique-view face image shown in FIG. 2A, at least 50% of the image pixels should belong to skin pixels. The Hu reference describes how to incorporate this information into the Otsu-based segmentation method. After the optimal threshold is computed from the thresholding algorithm, pixels whose ITA values are smaller than this threshold are classified as skin pixels. Thereafter, a binary (black-and-white) image is generated in which skin pixels are shown in white and non-skin pixels are shown in black.

Alternatively, the segmentation at 313 can be carried out with a thresholding method that uses a fixed threshold for a particular skin type to separate skin and non-skin regions where the fixed-threshold is determined, for example, based on skin data for the general or selected categories of population.

It should be noted that the skin map generation process of FIG. 3 can be carried out, with some modification, using an L*a*b* color space skin image 101A instead of an RGB image. In such an embodiment, the LUX transformation at 303 can be eliminated and the crude skin segmentation can be performed at 305 in the L*a*b* color space as described in the reference by S. L. Phung, A. Bouzerdoum, D. Chai, "Skin Segmentation Using Color Pixel Classification: Analysis and Comparison", IEEE Transactions on Pattern Analysis and Machine Intelligence, Vol. 27, No. 1, pp. 148-154, 2005. Advantageously, the transformation at 307 is also eliminated.

The segmented skin regions generated at 313 may include small, isolated areas that are markedly different in color than the rest of the skin, such as moles, scabs, scars, dense hair, or the like. Such areas may be eliminated at 315 by a morphological closing operation using a disk structural element or other such techniques. For a 220 PPI resolution image, for example, the diameter of this disk can be approximately 10 pixels (with a range of approximately 8 to 12 pixels being suitable). Alternatively, there may be skin patches detected in non-skin facial features (such as eyebrows, hair, etc.) These small patches are also eliminated with a morphological opening operation at 315 using the same disk structural element. Furthermore, some images may contain larger areas of non-skin-colored patches. These can also be eliminated by applying a morphological filling operation at 315.

The goal is to obtain a smooth and contiguous skin map from this operation. For example, for a typical oblique-view facial image centering on the cheek (see FIG. 2A), the resultant skin map 105 is to include all skin regions but the eye regions, eyebrows, nostrils, and hair (including any mustache or beard), and is to exclude skin regions in shadows (i.e., neck, dark nasolabial folds, the far side of the face which is in the dark, etc.) The skin map 105 thus generated is ideal for performing skin mask design in accordance with the present invention.

Automatic Design of Skin Mask for Full-Face Images

While the exemplary embodiment of FIG. 1 is directed to the generation of a skin mask for an image of a particular skin site (e.g., cheek area), exemplary embodiments will now be described for the generation of skin masks for full-face images, whether front- or oblique-view. The design of skin masks for sub-regions of the face will also be described.

Full-face images not only contain skin regions but also other facial features (e.g., eyes, eyebrows, hair, mustache, beard), thereby complicating the generation of a generic skin mask for any given face image. Such considerations are addressed by the embodiments described herein.

Figure 4:
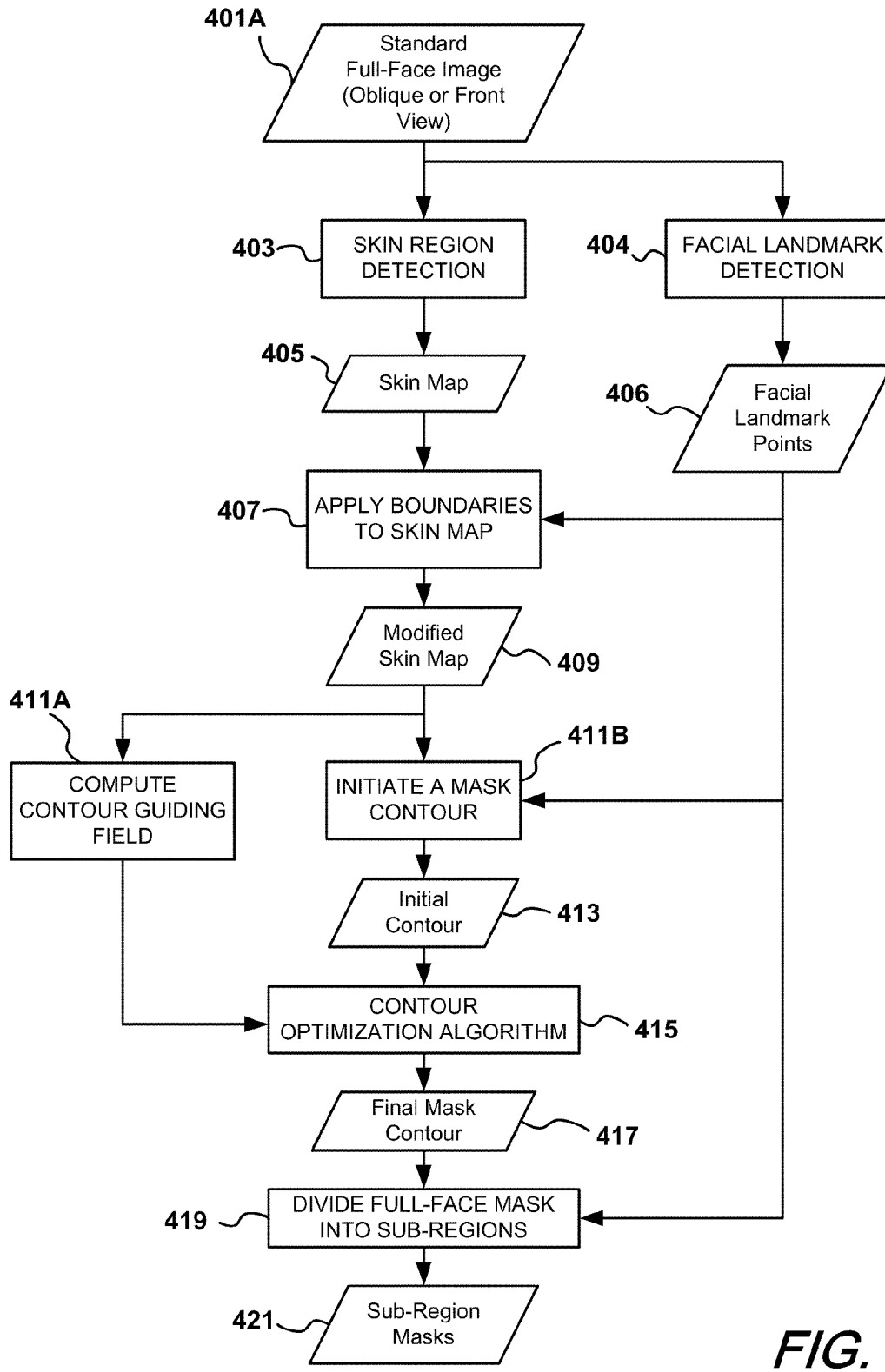
FIG. 4 is a high-level flowchart of an exemplary skin mask design method for full-face skin images utilizing the coordinates of a set of facial landmark points, in accordance with the present invention.

FIG. 4 is a high-level flowchart of an exemplary embodiment of a skin mask design method for full-face images. The full-face embodiment of FIG. 4 differs from the skin site embodiment of FIG. 1 primarily in the implementation of user-defined boundaries. Instead of using masking guidelines (101B), facial landmark points are detected and used explicitly to refine the skin map obtained from the skin region detection process.

Figure 5B:
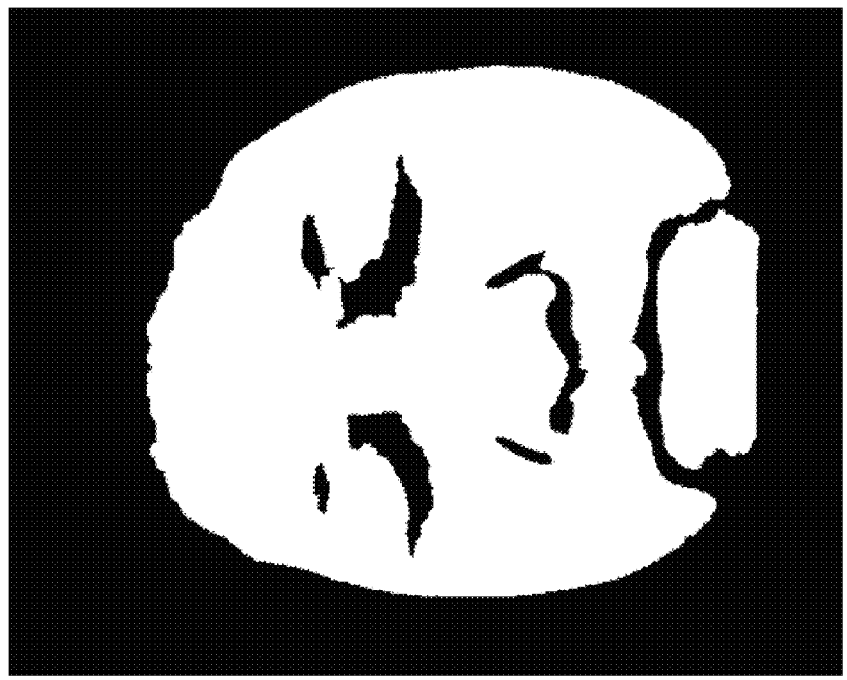
FIGS. 5A-5F show exemplary full-face front-view images relating to the exemplary method of FIG. 4.
Figure 5A:
Figure 9B:
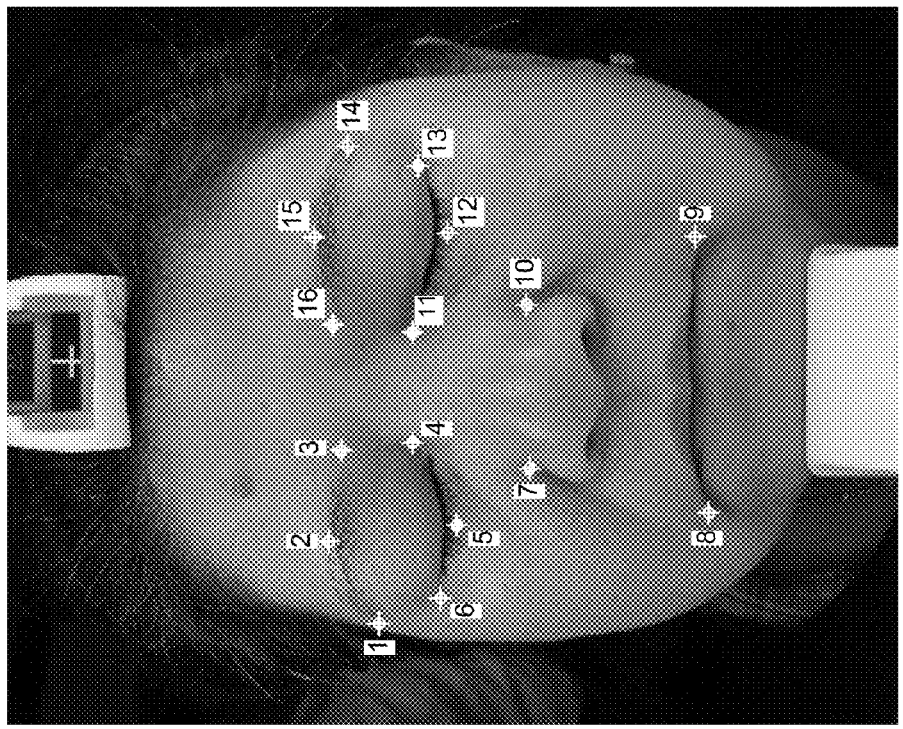
FIGS. 9A and 9B show illustrative front-view facial images and FIGS. 9C and 9D show illustrative oblique-view facial images with a corresponding set of detected facial feature points.

The process of FIG. 4 takes as an input a full-face, front- or oblique-view image 401A preferably captured under standardized and reproducible illumination and pose conditions. Face images can be captured from an oblique view (e.g., 45 to 90 degree angles) covering the left or right side of the face or from a frontal view symmetrically covering the full face. An illustrative full-face, front-view image is shown in FIG. 5A and an illustrative full-face oblique-view image is shown in FIG. 9C.

At 403, skin region detection, such as described above, is applied to the face image 401A to detect skin regions useful for computer analysis. This procedure returns a skin map 405 in which the final skin mask is to be designed. An exemplary skin map 405 for the image displayed in FIG. 5A is shown in FIG. 5B.

At 404, facial landmark points 406 are detected based upon the shape of the desired skin ROI. The landmark points are used to refine the skin map 405. They may be used to set hard boundaries or provide control points for the user-defined boundaries for a mask intended for a skin region of interest. Exemplary landmark points may include the endpoints of the eyes, eyebrows, lips and nose, among others. See, for example, FIG. 5C. Other or additional facial landmark points can be used depending on the desired skin ROI. Note that the set of landmark points and their locations detected for a front-view face image may differ from those of landmark points detected for an oblique-view face image. FIGS. 9B and 9D show landmark points detected for illustrative front- and oblique-view images, respectively. Exemplary facial landmark detection methods are described in greater detail below.

At 407, using the set of facial landmark points 406, boundaries are applied to the skin map 405 to obtain a modified skin map 409 in accordance with the desired front-view skin ROI. This is similar to the procedure (107) described above for the exemplary method of FIG. 1.

Figure 5D:
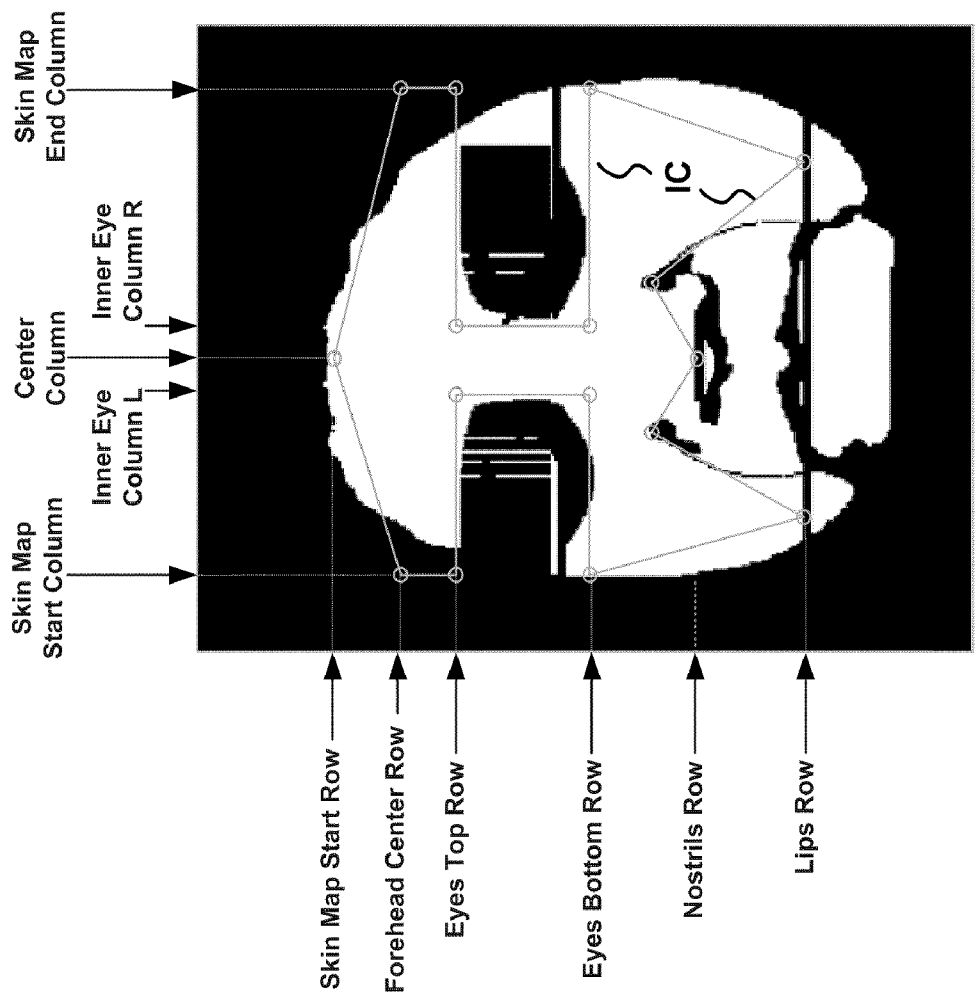
Figure 5C:
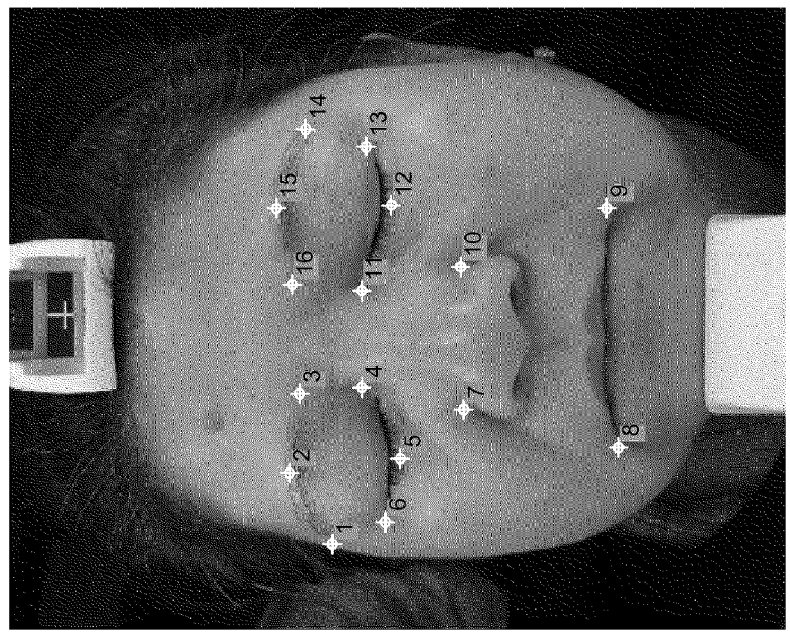

The method of FIG. 4 then proceeds as described above for the method shown in FIG. 1. At 411B, an initial contour 413 is designed based upon the landmark points and the modified skin map 409. An exemplary initial contour is shown in FIG. 5D as a polygon IC. The vertices of this polygon are automatically determined based upon the landmark points 406 and outer borders of the modified skin map 409. The row and column coordinates of these vertices are marked in FIG. 5D. These rows and columns are estimated based upon the landmark points and borders of the skin map. For example, the top vertex of the polygon IC is the intersection of the skin map start row and the skin map center column. The skin map start row is determined by scanning row-wise down from the top of the skin map. If the number of white pixels in a row exceeds some proportion (e.g., 10%) of the total number of pixels in the row, the row is treated as the skin map start row. The skin map center column can be determined as the column mid-way between the left and right inner eye columns, which in turn, correspond to the columns of the respective inner eye endpoints (which can be determined as described below in greater detail).

The skin map start column is determined by scanning the skin map 409 column-wise starting from the left border. If the number of white pixels in this column exceeds some portion (e.g., 10%) of the total number of pixels in the column, this column is designated to be the skin map start column. The skin map end column is found in similar fashion by scanning the skin map column-wise starting from the right border.

The nostrils row is determined by row-wise scanning the skin map in between the column coordinates of landmark points 7 and 10 (see FIG. 5C), starting from the lower of the row coordinates of points 7 and 10. If the number of dark pixels in a row and between the aforementioned columns exceeds a predefined threshold (e.g., 10 pixels), the row is treated as the nostrils row.

The lips row, eyes top row, eyes bottom row, inner eye column left and inner eye column right are determined based on their associated landmark points. Methods for detecting landmark points are described below.

It is important to note that the initial polygon shown in FIG. 5D is one in many possible alternatives. The initial contour 413 is preferably placed in close proximity to the landmark points and borders of the modified skin map so that an active contour optimization algorithm can converge to a global solution (i.e., yields a contour outlining the boundaries of the skin map).

At 411A, a contour-guiding potential field based upon the boundaries of the modified skin map 409 is computed. As in the embodiment of FIG. 1, the contour-guiding potential field is used to drive the initial contour 413 to the true boundaries of the object.

Figure 5F:
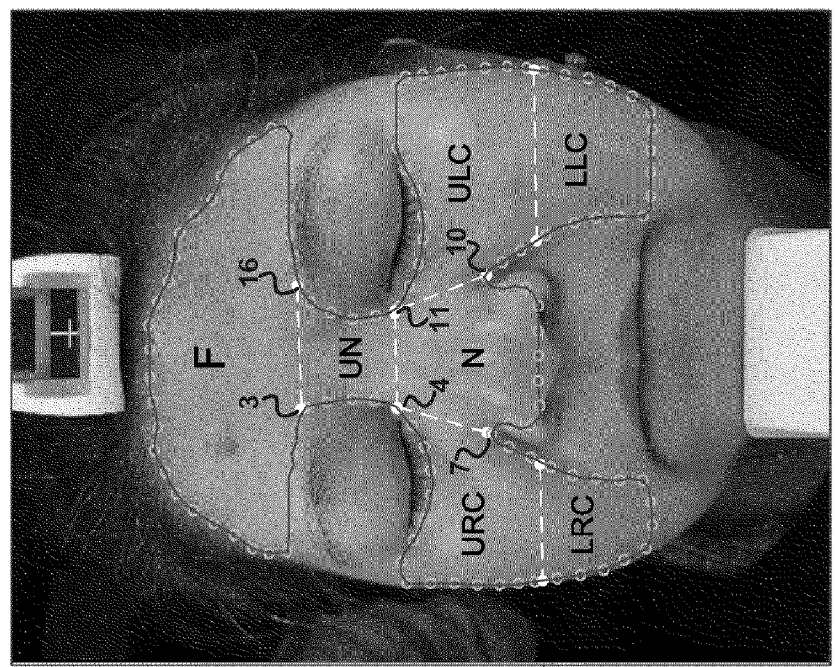
Figure 5E:
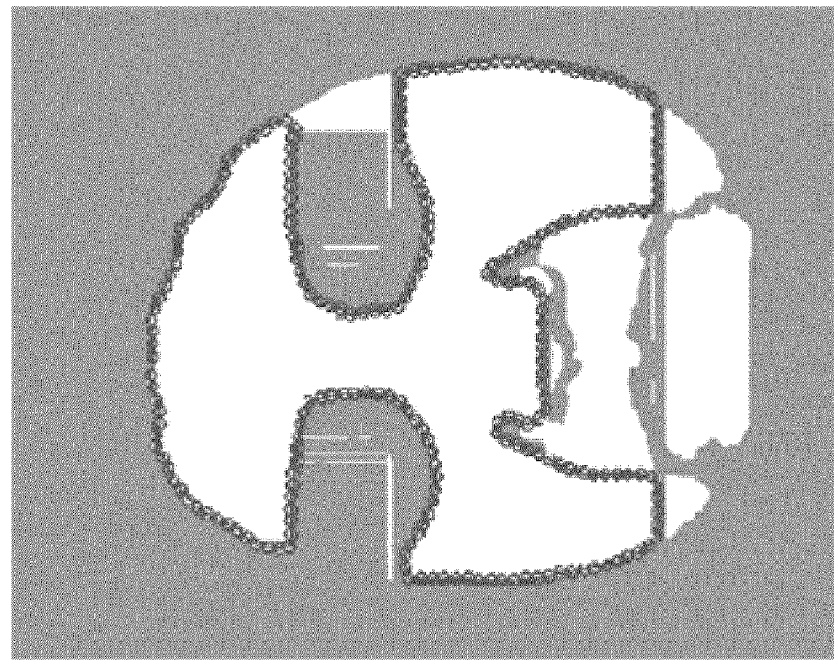

At 415, a contour optimization algorithm takes the initial contour 413 and drives the contour to the true boundaries by optimizing an energy functional based upon the contour-guiding potential field computed at 411A and regularity terms for the smoothness and integrity of the contour. The contour optimization algorithm carried out at 415 can be the same as that described above in connection with the embodiment of FIG. 1. It takes the initial mask, evolves to object boundaries, and returns the final mask contour 417. An exemplary final mask contour is shown in FIG. 5E overlaid on the original image as a chain of points. This mask covers most skin regions down to the lips level and follows the natural boundaries of the face. Optionally, as described above for the embodiment of FIG. 1, a graphical editing capability can be provided to allow a user to modify the final mask contour 417.

At 419, the mask contour 417 can be divided into a set of exemplary sub-regions using some of the available landmark points. The landmark points used for obtaining these exemplary sub-regions are marked in FIG. 5F using the same labels as in FIG. 5C. These sub-regions, namely the forehead (F), upper-nose (UN), nose (N), upper left-cheek (ULC), lower left-cheek (LLC), upper right-cheek (URC), and lower right-cheek (LRC) are shown in FIG. 5F. The upper and lower cheek regions are separated by the nostrils row. Some neighboring sub-regions can be combined to obtain a larger sub-region if desired. For instance, the sub-regions upper left cheek (ULC) and lower left cheek (LLC) can be combined to obtain a left-cheek mask. Each sub-region could be useful for a specific type of analysis. For example, one may want to apply wrinkle or texture analysis on the forehead (F) region, and pigmentation analysis on the cheek regions.

The sub-regions illustrated are only a few instances of all possible sub-regions. One can design a sub-regional mask for a specific part of the face given the methods explained above.

Facial Landmark Detection

Facial landmark points provide important clues for identifying faces and sub-regions of the face. They also can be utilized as guidelines in designing facial skin masks with sub-regions based upon the detected landmark points. As described above with reference to the exemplary method of FIG. 4, a set of landmark points for a full-face image are automatically detected as part of an automatic skin mask design process. Landmark points can also be detected automatically to assist with the user-directed or manual design of a skin mask as well. Automatic and reliable detection of these points are not only useful for mask design but also for identifying specific regions of the face, estimating the orientation and rough coverage of the face, and registering face images, among other uses. Methods for detecting facial landmark points, such as those above, will now be described.

Figure 6:
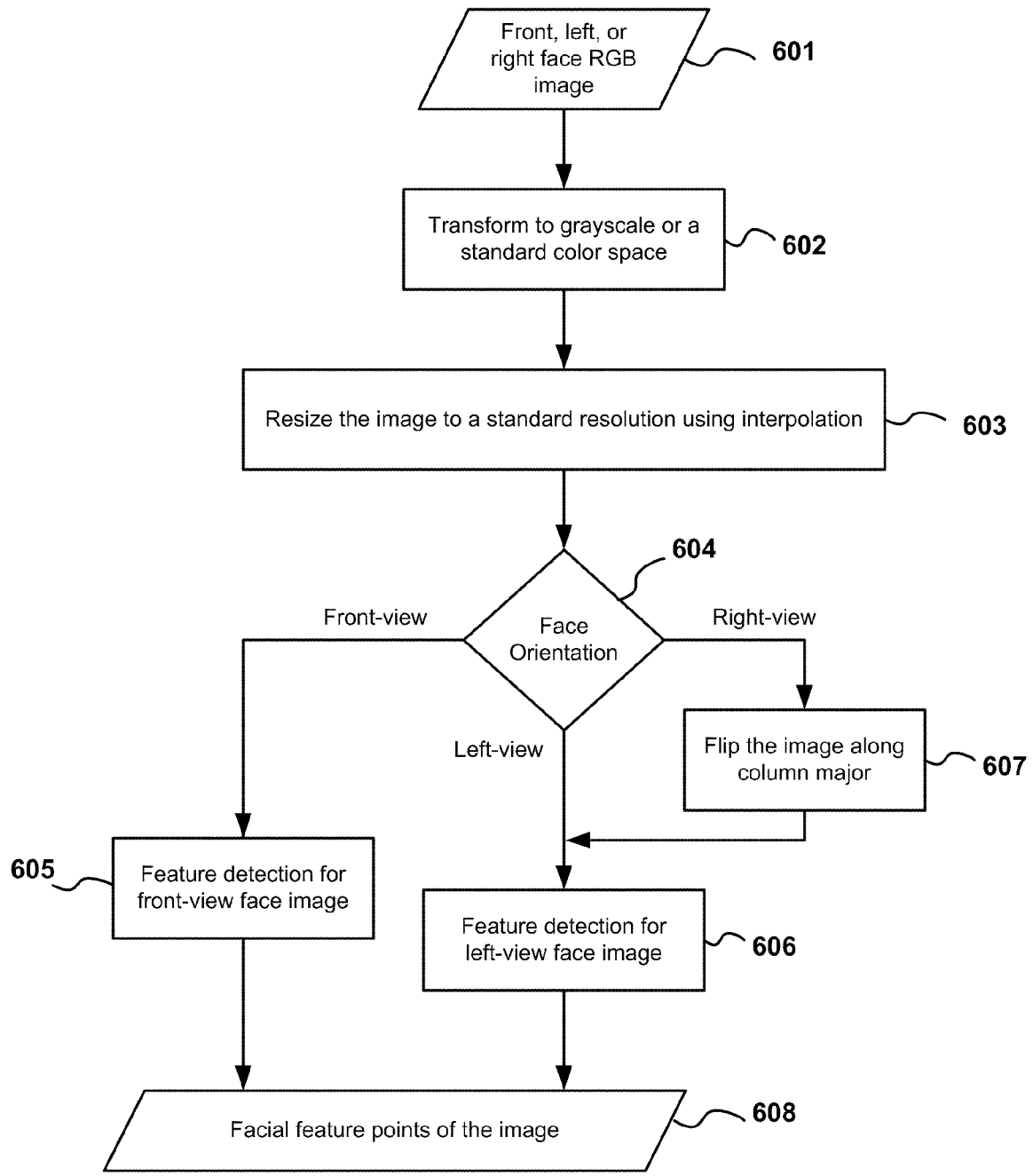
FIG. 6 is a high-level flowchart of an exemplary method for determining facial orientation in an image and branching to a specific facial feature detection mode for the orientation, in accordance with the present invention.

FIG. 6 is a flowchart of an exemplary process for automatically extracting key feature points in facial images with various orientations. The images can be full-face images or images of portions of the face targeting skin sites of interest (e.g., cheek area). An RGB front- or oblique-view face image 601 is transformed at 602 into a grayscale image or any standard color space (for example, HSV, CIE L*a*b*, etc.) A component of any of the color spaces or one or more combinations of various components from the same or different color spaces is used to detect the feature points. Preferably, for the sake of computational efficiency, the image is resized at 603 to a standard resolution by interpolation schemes such as bilinear or bicubic interpolation or the like.

At 604, a suitable manual, automatic or semi-automatic mechanism or procedure can be used to determine the orientation of the face in the image 601 for subsequent processing of the image as a front, right, or left face image. If the image is determined to be a front face image, then a procedure is carried out at 605 to detect the key facial feature landmark points. Such a procedure is described in greater detail below with reference to FIGS. 7A and 7B. If the image 601 is determined at 604 to be a left face image, then the procedure at 606 is carried out, described in greater detail below with reference to FIGS. 8A and 8B. If the image 601 is a right face image, then the image is transposed at 607 along the columns (e.g., the image is flipped horizontally) and processed as a left face image at 606. After the feature points are detected at 606, the points are transposed back for right face images.

Figure 7A:
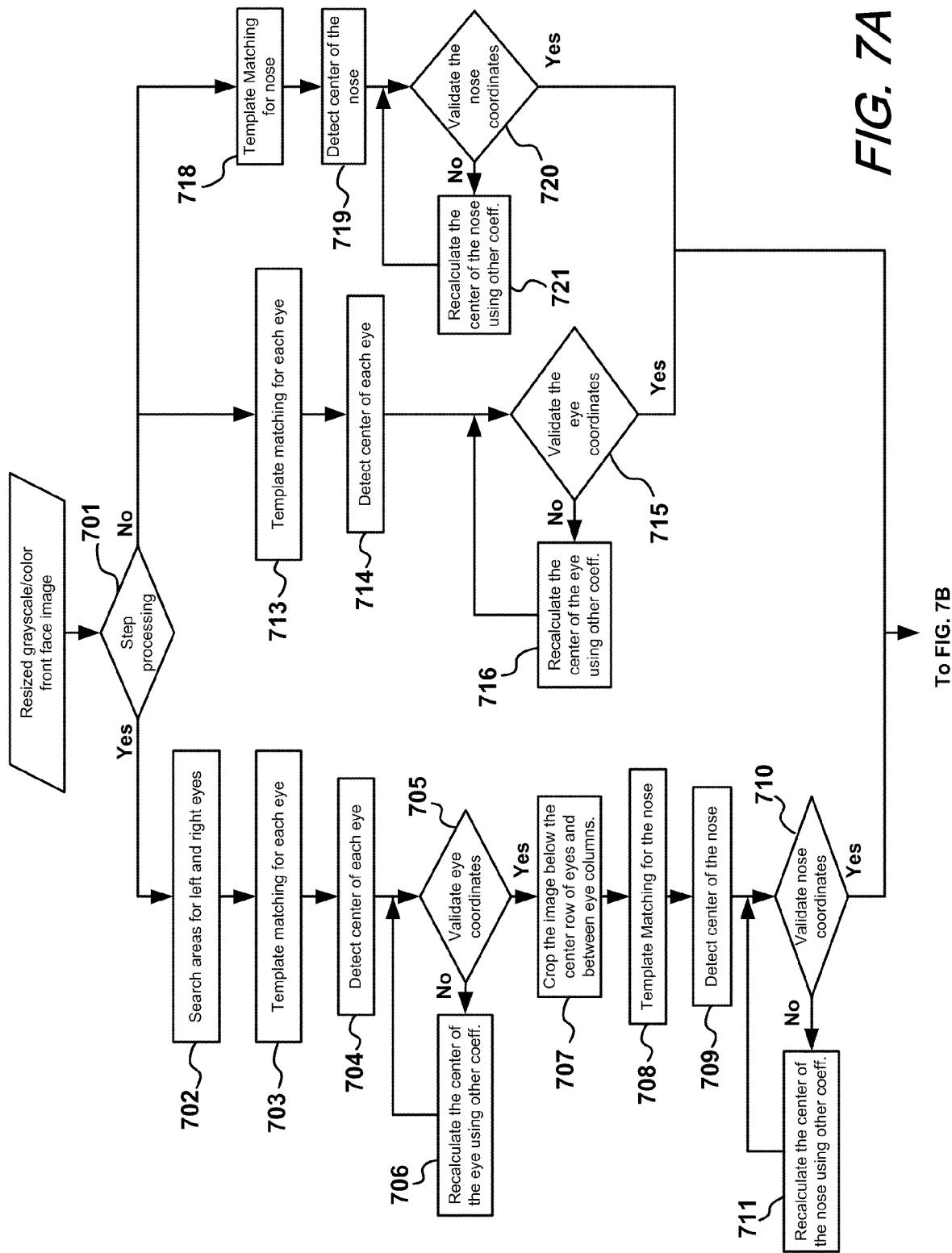
FIGS. 7A and 7B show a high-level flowchart of an exemplary method of detecting a set of exemplary facial feature points for a front-view facial image.
Figure 7B:
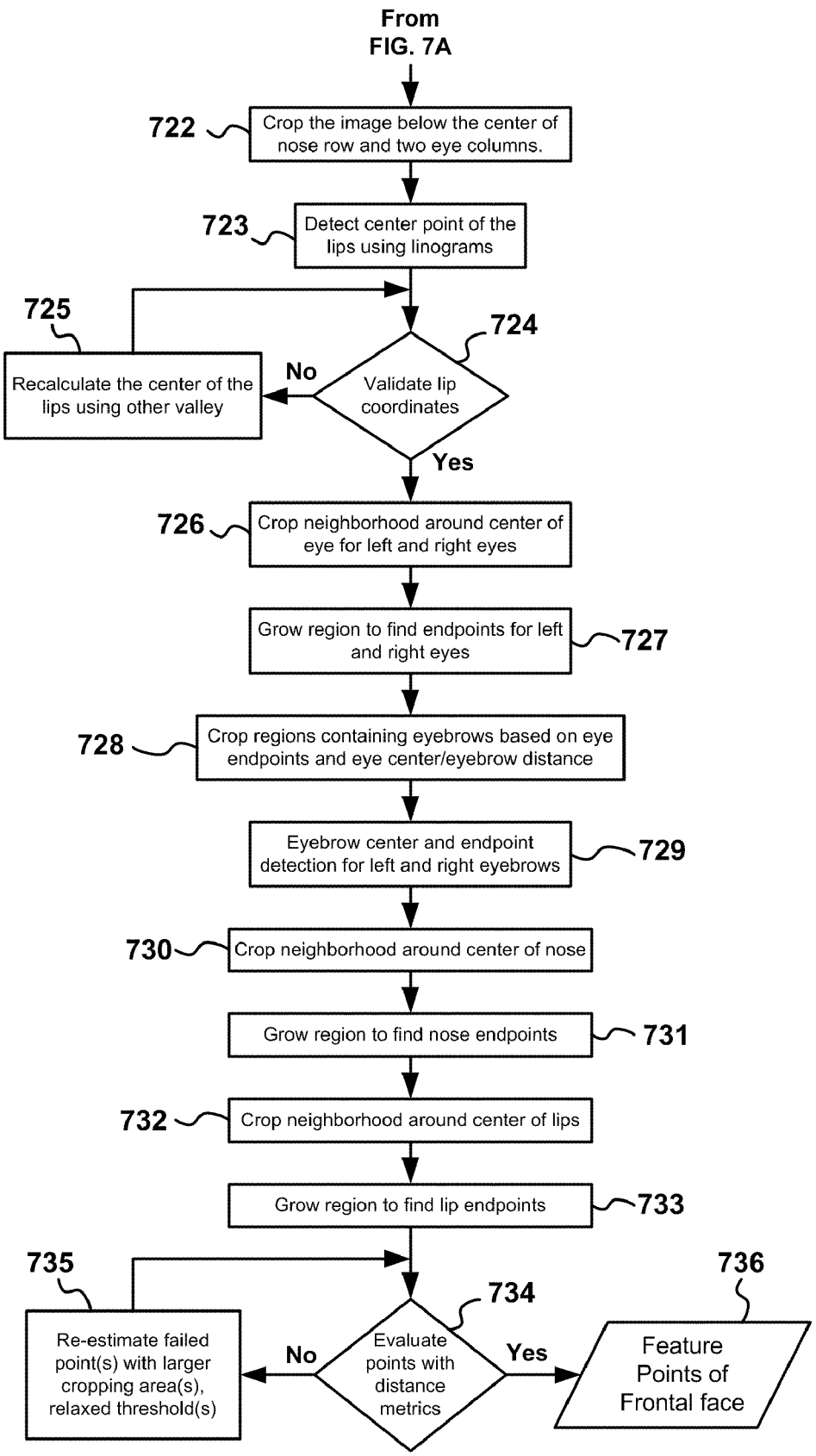

FIGS. 7A and 7B show a high-level flowchart illustrating an exemplary embodiment of a method for detecting facial feature landmark points for front-view images. The method uses the resized, grayscale or standard color space image generated in the process of FIG. 6 at 603. As determined at 701, the exemplary feature point detection method shown can run in step processing mode or not. Step processing mode assumes that the face in the image is in an upright position, so that when traversing the rows of the image from top to bottom, the eyes are encountered first, followed by the nose and lips. Images of faces with a high degree of asymmetry or in which the face is rotated can be processed using the non-step processing mode where feature detection is done in the entire image without a hierarchical order.

In either mode, the feature points are detected in a two-stage approach. In the first stage, the center points of the eyes, lips, and nose are detected. As described below, the center points of various features can be detected by a template matching approach. In the second stage, these points are grown using statistical measures (e.g., mean, standard deviation, etc.) to find the endpoints of the features. Instead of thresholding and segmenting the whole image, sub-regions are automatically identified and different thresholding and segmentation algorithms are applied to each of these sub-regions to find the feature points of interest. This approach gives the flexibility to detect points around the features with greater accuracy than the generic thresholding-based approach proposed in A. Yilmaz and M. Shah, "Automatic Feature Detection and Pose Recovery of Faces", The 5th Asian Conference on Computer Vision, 23-35, January 2002, Melbourne, Australia.

When operating in step processing mode, searches are performed at 702 for the left and right eyes. These searches can be carried out in parallel or sequentially. Preferably, features are detected in a specific order depending on their importance and ease of detection. By limiting the search areas for each feature, computational complexity is reduced. For example, in 702, the eyes are searched for within the upper two-thirds of the rows of the image. Assuming a generally symmetric face, the left eye is searched for in the first half of the columns of the image and the right eye is searched for in the second half of the columns of the image. (Note that when referring to a facial image herein, the terms "left" and "right" are with reference to the viewer of the image and not the subject of the image. Moreover, the first column of the image refers to the leftmost column of the image whereas the last column refers to the rightmost column of the image.) For asymmetric face images, the search areas for the eyes can be appropriately modified or the search skipped, as in the non-step processing mode.

Figure 7C:
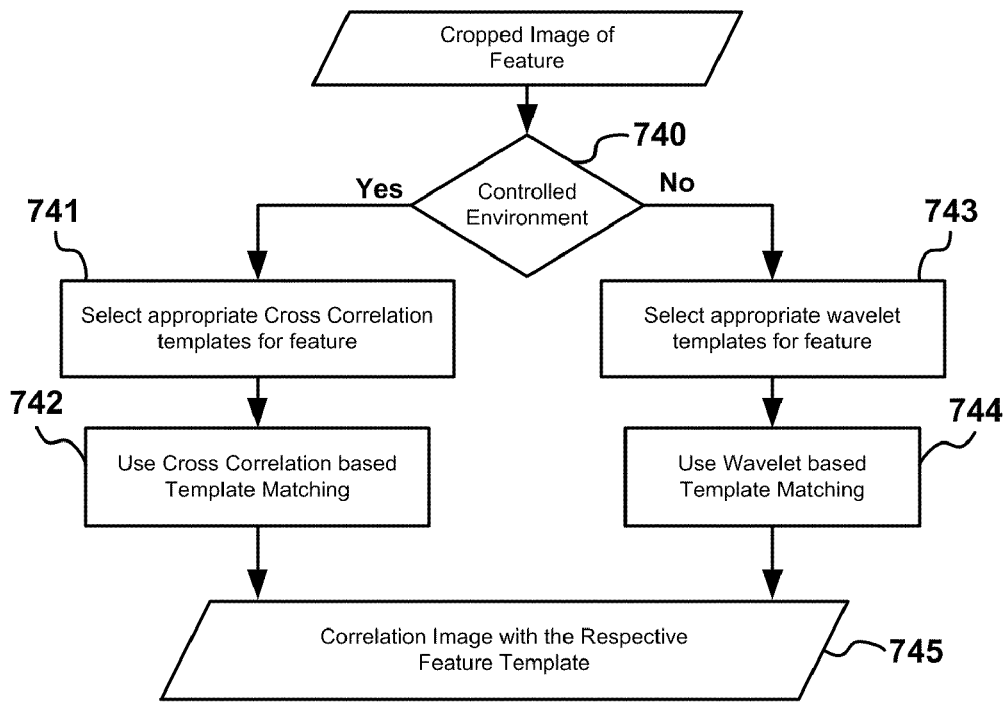
FIG. 7C is a flowchart of an exemplary template-matching technique for the detection of a specific feature.

Once the left and right eyes have been found in 702, a template matching procedure is performed at 703 to detect the center of each eye. Such a template matching procedure is shown in FIG. 7C. The template matching procedure determines how well a pattern of gray intensities (a template) matches a similar pattern in the given image. Controlled image capture environments are not expected to introduce high variations in scale and orientation. If the subject image was captured in such an environment, as determined at 740, operation proceeds to 741 in which an appropriate cross correlation template is selected for the facial feature (e.g., right eye, left eye, nose) to be matched. The selected template is used at 742 to perform normalized cross-correlation-based template matching. For uncontrolled image capture environments (e.g., image is a frame in a video sequence), operation proceeds to 743 in which an appropriate wavelet template is selected and used in 744 to perform wavelet-based template matching in which single or multiple templates with different orientations and scales may be used. The template may be selected, for example, from a library of templates which generically represent the various facial features to be matched, with variants for different skin types and feature sizes, among other parameters. Such a library may also include templates in a variety of color spaces for matching features in facial images in different color spaces.

The template matching procedure of FIG. 7C returns a correlation image 745 with the template of the feature to be matched.

Referring again to FIG. 7A, at 704, the point at which the correlation coefficient is at a maximum in the area of search for an eye is deemed to be the center of the eye. Statistical measures such as mean or median in combination with distance metrics can be used to determine the point of maximum correlation, as proposed by R. Brunelli and T. Poggio, "Face Recognition: Feature versus Templates," IEEE Transactions on Pattern Analysis and Machine Intelligence, Vol. 15, No. 10, pp. 1042-1052, 1993.

Figure 14:
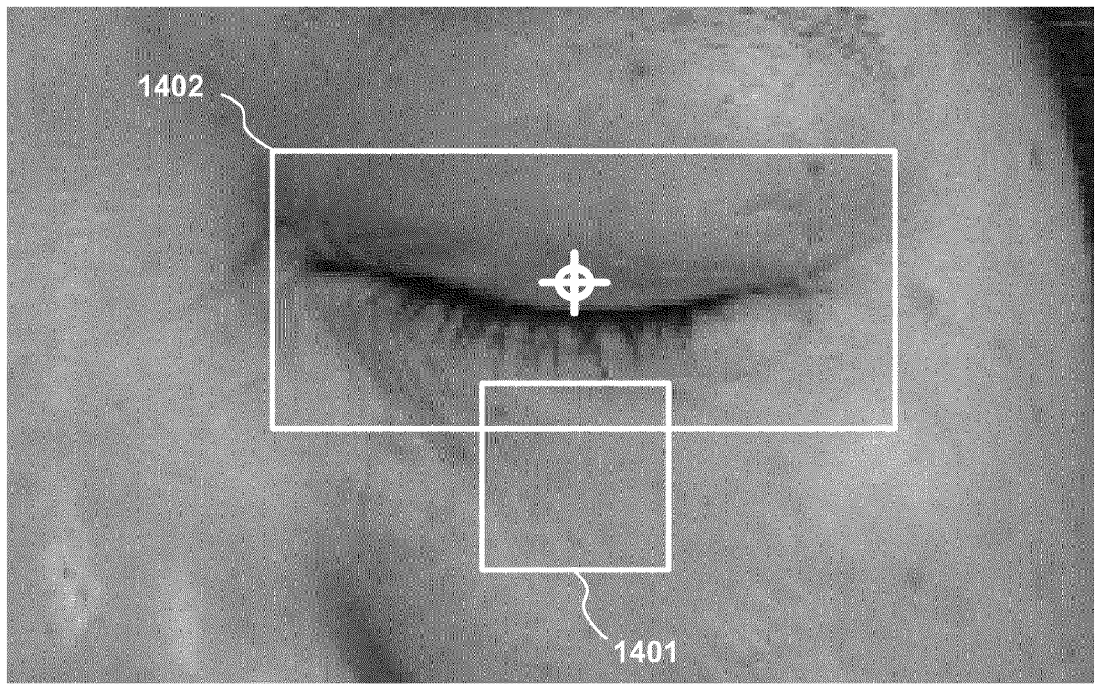
FIG. 14 is a close-up view of an eye illustrating windows around the eye and upper cheek area used to validate the center point of the eye using a statistical model in accordance with the present invention.

Using an iterative procedure at 705 and 706, the coordinates of the center of each eye as detected at 704 are validated using a statistical model. Typically, the upper cheek region below the center of the eye has a light skin tone compared to the rest of the face. Such variations in skin tone are used for validating the center of each eye at 705 and 706. As shown in FIG. 14, in accordance with an exemplary embodiment, a first, small window 1401 (e.g., 10×10 pixels for a 220 PPI resolution image), is selected a few rows below the detected center of the eye in the upper cheek region, and a second, larger window 1402 (e.g., 20×40 pixels for a 220 PPI resolution image) is selected around the center of the eye. The mean intensity of all pixels in each window is computed. If it is determined at 705 that the mean intensity in the window 1401 is greater than the mean intensity in the window 1402, the coordinates of the center of the eye are deemed to have been validated and a detection accuracy score for the eye is set to a first value, e.g., 1. If, however, it is determined at 705 that the mean intensity in the window 1401 is less than the mean intensity in the window 1402, then at 706 a new point is selected as the eye center. The new point is the point at which the correlation coefficient calculated above has its next highest value. The new point is then re-validated against the model at 705 and if the model is satisfied, the new point is treated as the eye center point. In this case, the detection accuracy score for the eye is set to a second, lower value, e.g., 0.5. If the validation model is still not satisfied, the procedure at 705 and 706 is repeated using the point with the next highest correlation value until the point that satisfies the validation model is found. For such points, the detection accuracy score can be set to the second value or it may be based, for example, on the point's correlation value. The same procedure can be used to validate the centers of both the left and right eyes.

After the centers of the eyes have been detected and validated, as described, the center of the nose is detected next, starting with 707. At 707, the search area for the nose is preferably limited—thereby reducing computational complexity—to rows below the center row(s) of the eyes. If the detection accuracy of the centers of both eyes is 1, as determined above, the nose search area is limited to the columns between the two eye centers. If, however, the detection accuracy for only the left eye is 1, then the nose search area is limited to the columns from the center of the left eye to the last column of the image (i.e., the right edge of the image). Similarly, if the detection accuracy for only the right eye is 1, then the nose search area is limited to the columns from the first column of the image (i.e., the left edge of the image) to the center of the right eye. If the detection accuracies of both eyes are less than 1, then all columns of the image are searched.

At 708, template matching using a predetermined nose template is performed on the nose search area determined in 707, as described above. The template matching technique used can be the same as that used for the eyes, as described above with reference to FIG. 7C. At 709, the location of the point of maximum correlation between the template and the search area is deemed to be the center point of the nose.

Figure 15:
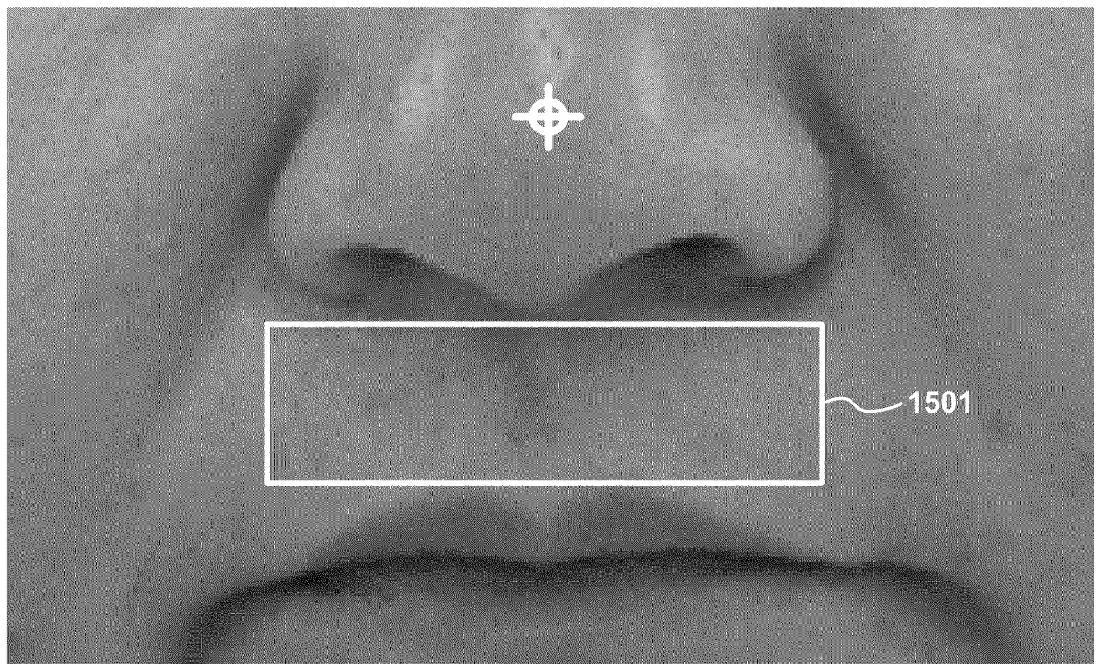
FIG. 15 is a close-up view of the nose and lips illustrating a window used to validate the center point of the nose using a statistical model in accordance with the present invention.

Using an iterative procedure at 710 and 711, the coordinates of the center of the nose as detected at 709 are validated using a statistical model. The region below the tip of the nose and above the lips has a larger gradient strength compared to the skin or the lips. Gradient is representative of the difference in intensity between a pixel and its horizontal or vertical neighbors. The variation in gradient strength is used as a measure to validate the nose center point at 710. A combined gradient image is obtained by applying horizontal and vertical gradient mask filters to the cropped nose image. As shown in FIG. 15, in accordance with an exemplary embodiment, a window 1501 generally covering the area below the nose and above the lips (e.g., 10×40 pixels for a 220 PPI resolution image) is selected in the combined gradient image a few rows below the nose center point to be validated. The mean gradient strength in the window 1501 is computed and if it is above a predetermined threshold, the point is confirmed to be the nose center point. An appropriate value for the threshold can be determined empirically, for example, using multiple facial images, preferably for different skin types. If, however, the mean gradient strength in the window 1501 is not above the predetermined threshold, the center point of the nose is recalculated at 711 using the next highest correlation coefficient until the condition is satisfied at 710.

The non-step processing mode of operation (as determined at 701) follows a similar sequence as that described above for the step processing mode. In this mode, template matching and center detection is carried out for each eye at 713 and 714, respectively, and for the nose at 718 and 719, respectively. The eyes and nose can be processed in parallel or sequentially. The validation of the eye and nose center point coordinates are carried out by iterative procedures at 715 and 716, for the eyes, and 720 and 721, for the nose, similar to those described above.

Once the centers of the eyes and nose have been detected and validated, operation proceeds to 722 (FIG. 7B) to locate the center of the lips. In an upright image the lips are located below the nose. At 722 the search area for the lips is limited to the rows below the row of the nose center point. Furthermore, if the detection accuracy of the center of the right eye is 1, then the columns of the image to the right of the center of the right eye can be excluded from the search area for the lips. If the detection accuracy of the center of the left eye is 1, then the columns of the image to the left of the center of the left eye can be excluded from the search area for the lips.

At 723, a linogram is computed for the search area determined at 722. The linogram computed is the sum of intensities of the pixels in a row vs. the location of the row (or row number) along all the rows of the search area. In an exemplary embodiment, valleys in the linogram are detected based on changes in slope and the sensitivity of the valley detection is auto-tuned based on peak linogram strength. The first valley below the nostrils row is in the row between the upper and lower lips, or the lips row.

Figure 16:
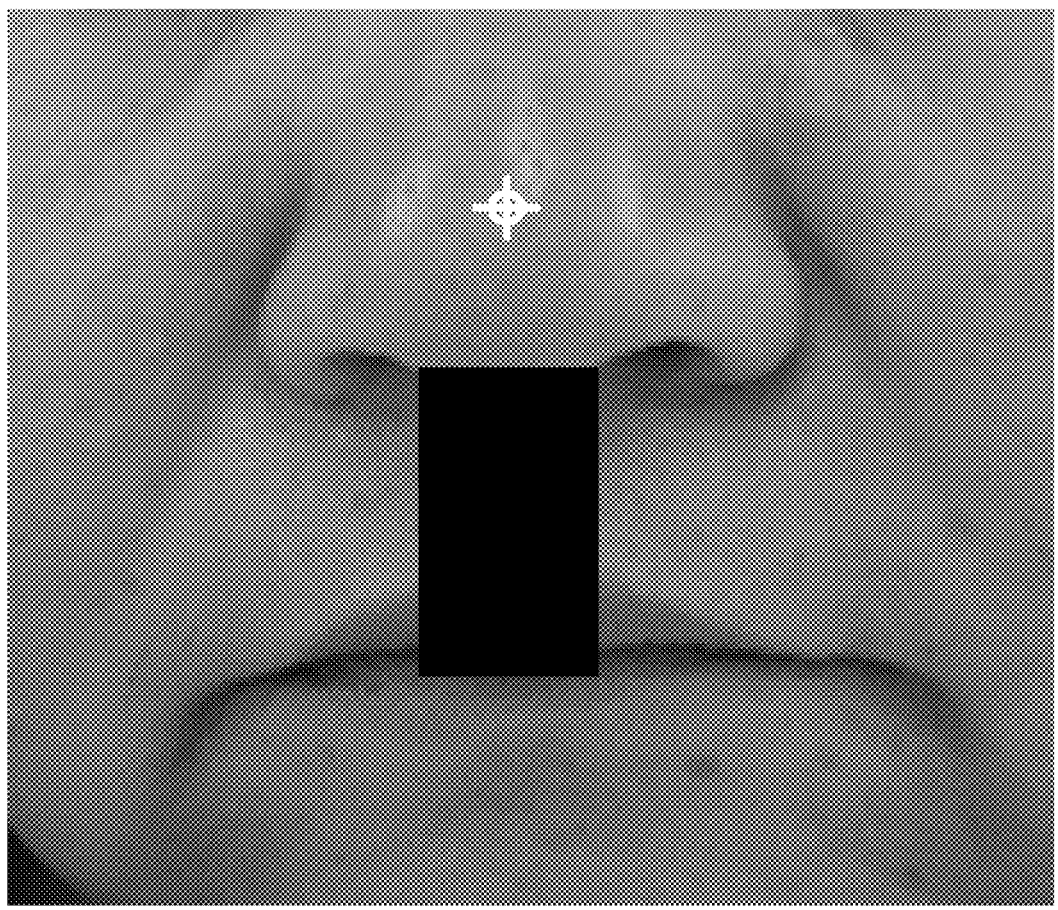
FIG. 16 is a close-up view of the nose and lips illustrating an area below the nose which is set to zero intensity in computing a linogram used to determine the center of the lips in accordance with the present invention.

Preferably, as depicted in FIG. 16, in order to eliminate or reduce the influence on the linogram that the nostrils may have—which in some subjects may be visible while in others not—a few columns of the image (e.g., 10 for a 220 PPI resolution image) on either side of the center of the nose up to a portion of each nostril, can be set to zero (i.e., set to black) before computing the linogram. Also, as shown in FIG. 16, this blackened region starts from around the nostrils line and preferably extends down to the lips, blackening some of the lips. This also improves the robustness of the linogram-based detection.

If the lips row is not between predefined boundaries for a given resolution, a default lips row is used which is a predetermined number of rows below the row through the center of the nose. Said predetermined number of rows can be determined, for example, from facial measurements of the general population, or preferably of a population category (e.g., sex, age, race) to which the subject belongs.

For most cases, the column of the center of the nose can be assumed to be the same as the column of the center of the lips, due to the symmetry of the face. The intersection of this column and the lips row can be treated as the center point of the lips.

Using an iterative procedure at 724 and 725, the coordinates of the center point of the lips determined at 723 are validated based on the distance of the center of the lips from the center of the nose. At 724, the point is validated as the center of the lips if its distance from the center of the nose is within a specified range, based, for example, on population facial measurements. If the validation fails, the next detected valley in the linogram is evaluated at 725 until the condition is satisfied at 724.

Figure 9A:
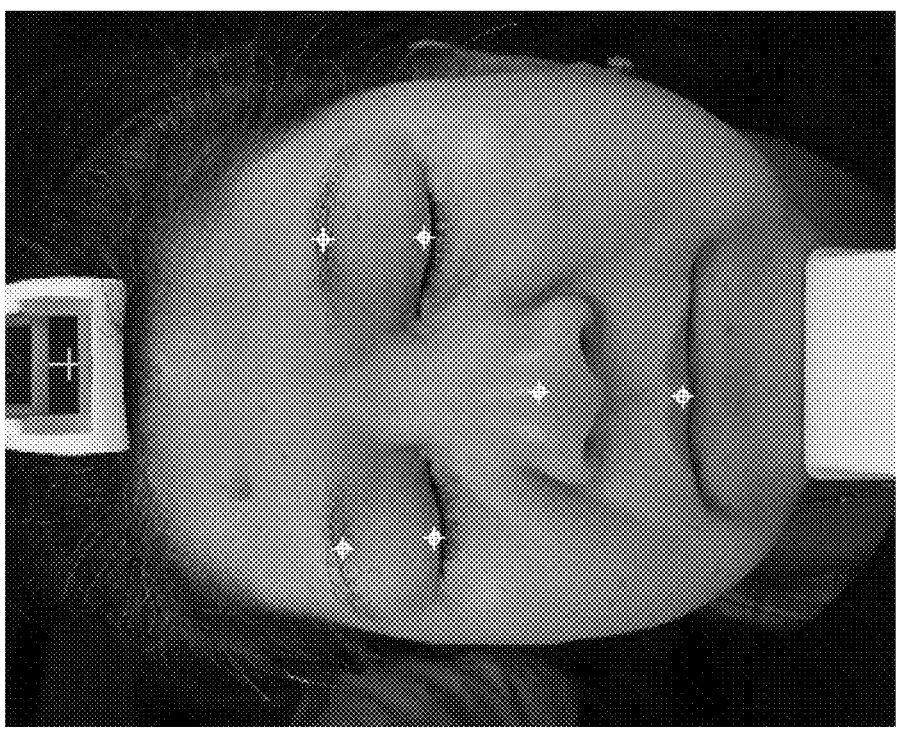
Figure 9D:
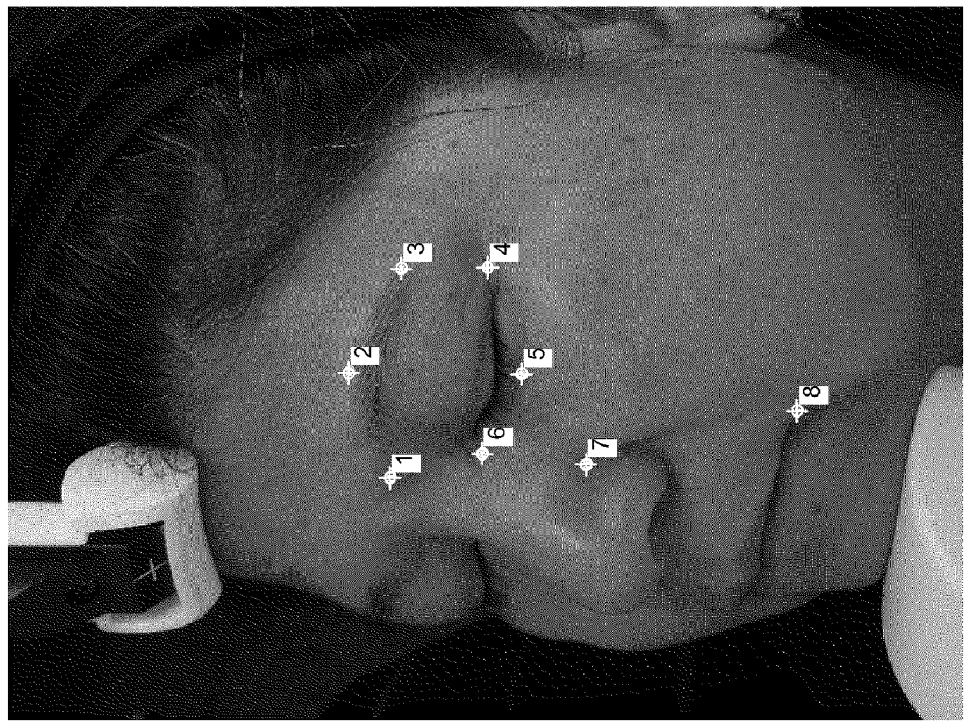
Figure 9C:
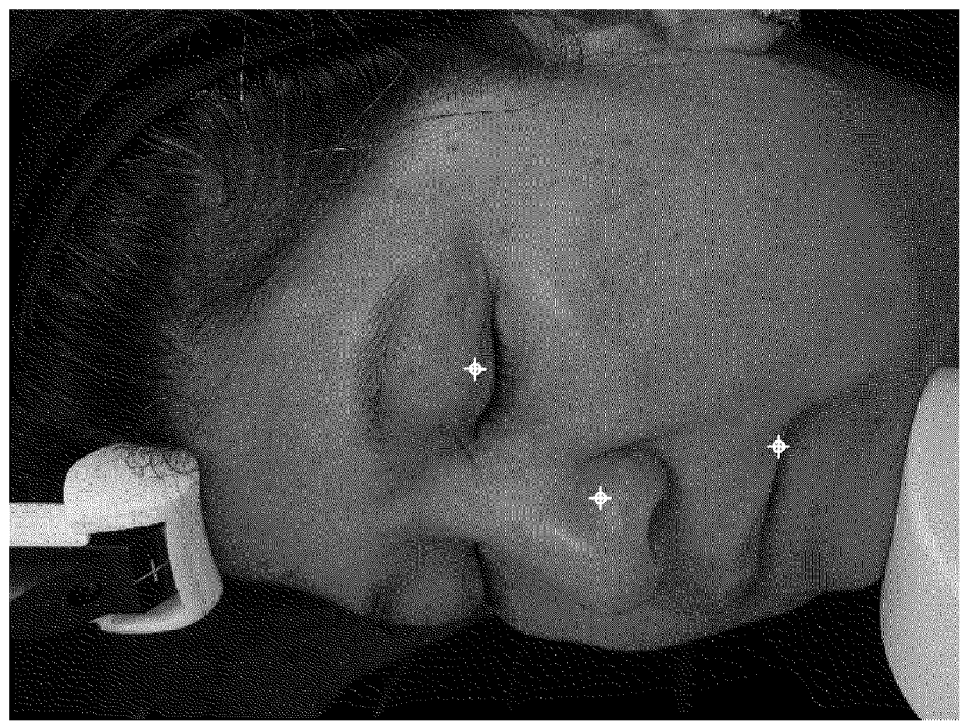

Illustrative results for the detected centers of the eyes, nose, and lips in a front-view full face image are represented in FIG. 9A by circles with crosshairs. Note that in the illustrative image of FIG. 9A, the eyes are closed. As such, the above-described template matching will be carried out using templates of closed eyes. As can be appreciated, for images with open eyes, templates of open eyes would be used.

Once the center points of the eyes, nose and lips are detected and validated, as described above, the endpoints of these features are found automatically by region growing techniques. These endpoints are later used to set boundaries for the skin map.

At 726, based on the centers of the eyes, a local neighborhood region is delineated for each of the left and right eyes. For a given resolution, the size of each region is estimated based on the width and height of each eye for the general population.

Figure 7D:
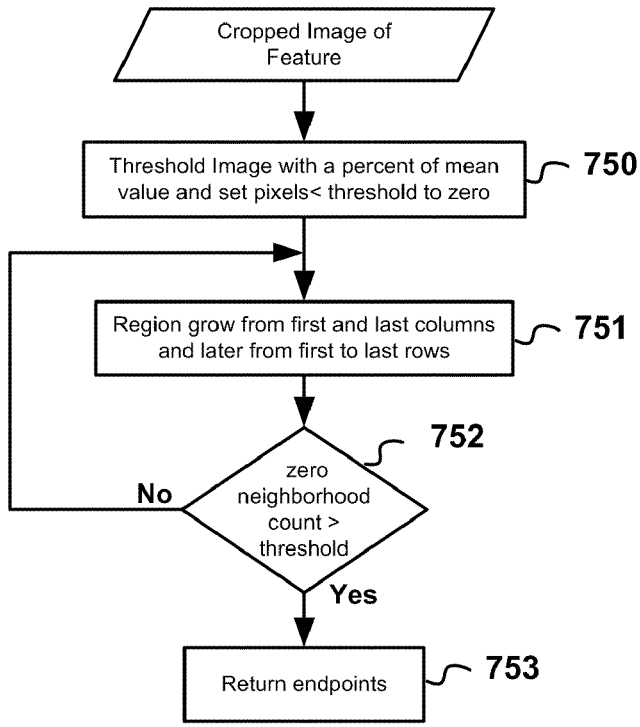
FIG. 7D is a flowchart of an exemplary region-growing technique for the detection of eyes and nose endpoints.

Operation then proceeds to 727 in which a region growing procedure is carried out to find the endpoints of each eye. This procedure is shown in greater detail in FIG. 7D. As shown in FIG. 7D, the local neighborhood region for the eye being processed (i.e., a cropped image consisting of the local neighborhood region) is mean thresholded at 750 by setting to zero intensity those pixels whose intensities fall below a percentage (e.g., 70-95%) of the mean intensity value of the local neighborhood region.

At 751, the endpoints of the eye are estimated by searching for zero-intensity pixels in the thresholded cropped image of the eye. To locate the column of the right endpoint of the eye, the search begins at the right edge (or last column) of the thresholded image and progresses to the left (towards the first column). To locate the column of the left endpoint of the eye, the search begins at the left edge (or first column) of the thresholded image and progresses to the right (towards the last column). At 752, the column of the thresholded image at which the cumulative number of zero-intensity pixels encountered in the search equals or exceeds a predetermined threshold is deemed to be the column of the endpoint searched for. An appropriate value for the threshold can be determined empirically, for example, using multiple facial images, preferably for different skin types.

To find the rows of the eye endpoints, the search begins at the top row of the thresholded image and progresses downward, toward the bottom row of the thresholded image. At 752, the row of the thresholded image at which the cumulative number of zero-intensity pixels encountered in the search equals or exceeds a predetermined threshold is deemed to be the row of the eye endpoints. Although the endpoints of an eye may be on different rows, for purposes of mask generation, the endpoints can usually be assumed to be on the same row. If, however, greater accuracy is required, the thresholded image of the eye can be divided (down the middle, for example) and each endpoint searched for individually using a similar approach.

With reference to the illustrative image of FIG. 9B, the procedure of FIG. 7D yields points 4 and 6 as the endpoints of the left eye and points 11 and 13 for the endpoints of the right eye.

Alternative methods such as a gradient filter in combination with thresholding or methods such as snakes (as proposed, for example, by K. M. Lam and H. Yan, "An Improved Method for Locating and Extracting the Eye in Human Face Images", Proceedings of the 13th International Conference on Pattern Recognition, Vol. 3, pp. 25-29, August 1996) can be used to find the endpoints of the eyes.

In addition to the eye endpoints, it may also be desirable to determine an additional point along the bottom of each eye (e.g., FIG. 9B, points 5 and 12) to better delineate the ultimate skin mask contour. A suitable location for each of these points is at the intersection of the column of the eye center and the bottom row of the eye. The bottom row of each eye can be found by searching in the thresholded cropped image of the eye for the highest row with all non-zero pixels below the lower of the rows of the eye endpoints (e.g., points 4 and 6, or 11 and 13). Alternatively, instead of locating these points and using them in the mask design, the generally arc-shaped curve between the eye endpoints can be estimated by a suitable curve fitting procedure.

Referring again to FIG. 7B, once the eye endpoints have been found at 727, the eyebrows are processed next, starting with 728. Eyebrow size, shape, and color vary from person to person, with women tending to have thin eyebrows and men thicker eyebrows. The exemplary method of the present invention takes into account such variations and detects the points of the eyebrows reliably. At 728, the eyebrows are isolated by cropping out an image of a region containing each eyebrow. The endpoints of the left and right eyes (e.g., points 4, 6, 11 and 13 in FIG. 9B) are used to delineate the regions containing the respective eyebrows. The heights of these regions can be selected, for example, in accordance with a statistical measure of the distance between the eye centers (or eye endpoints) and the eyebrows. Because this distance can vary considerably from person to person, the heights of these regions should be greater than those used above for the eyes. The widths of the eyebrow regions can also be selected, for example, in accordance with a statistical measure of the distance between the eye endpoints and eyebrow endpoints.

Figure 7E:
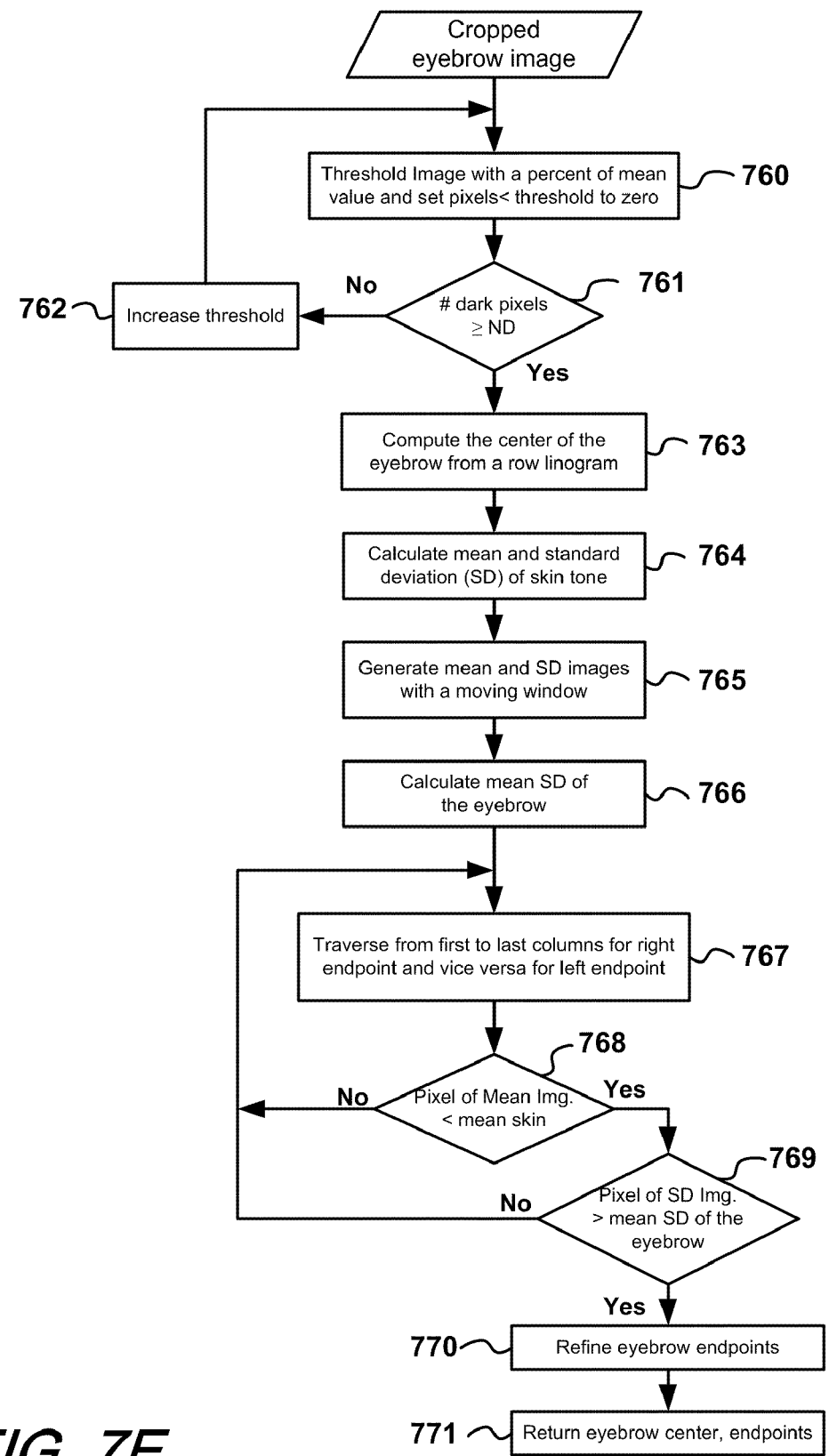
FIG. 7E is a flowchart of an exemplary region-growing technique for the detection of eyebrow endpoints, in accordance with the present invention.

Operation then proceeds to 729 in which the center point and endpoints of the left and right eyebrows are determined. A procedure for carrying this out will now be described in greater detail with reference to FIG. 7E. At 760, the mean intensity of all the pixels in the cropped eyebrow image (from 728) is computed and a percentage of that (e.g., 70-99%) is used to threshold the image by setting to zero the intensity of those pixels with intensities below the threshold. Because not all eyebrows are dark in color and some have almost the same color as the surrounding skin, thresholding the eyebrow pixels can be challenging. To address this issue, at 761 the zero-intensity or dark pixels in the thresholded image from 760 are counted and if the number of dark pixels counted is at least a predefined number ND (e.g., 50% of the total number of pixels in the cropped eyebrow image), then the thresholding is deemed complete and operation proceeds to 763. If the condition at 761 fails, however, the threshold is increased at 762 (e.g., the percentage of the mean intensity value of the cropped eyebrow image is increased) and the image is thresholded again at 760 using the new threshold. This procedure (760-762) is repeated until the total number of zero-intensity pixels is greater than the predefined zero-intensity pixel count.

At 763, the center point of each eyebrow is determined. The column of the center point of an eyebrow is determined by locating the top center point of the eyebrow. The thresholded image for each eyebrow, as generated above, is scanned from top to bottom along a few center columns (e.g., 30 columns on either side of the center of the thresholded eyebrow image for a 220 PPI resolution image) in search of a pixel with zero intensity. When such a pixel is encountered, it is treated as the top center point of the eyebrow (e.g., FIG. 9B, points 2 and 15) and its column is the same as that of the eyebrow center point.

To determine the row of the eyebrow center point, at 763, the sum of the intensities of all the pixels along each row in the thresholded eyebrow image is computed to generate a row linogram. The minimum value along the linogram corresponds to the row of the eyebrow center point. Illustrative eyebrow center points are shown in FIG. 9A.

Starting at 764, the endpoints of the eyebrows are then determined. The differences in the intensity variations and texture of skin and hair are used to segregate them. Skin tone is typically lighter than hair. Skin also tends to be more even than hair, which has more texture. At 764, the mean and standard deviation of the skin tone of the subject are computed using a first small window (for example, 3×3 pixels for a 220 PPI resolution image) from a portion of the cropped eyebrow image that contains only skin (e.g., the upper left corner for the right eyebrow, or the upper right corner for the left eyebrow). The standard deviation measure can be used (as described below) to correct for problems caused, for example, by deeper eye sockets as they tend to be darker than more exposed skin areas.

At 765, using a second window of the same size as the first window (e.g., 3×3 pixels), images for moving average and moving standard deviation are computed from the original cropped eyebrow image.

At 766, the mean of the standard deviation of the eyebrow is estimated by calculating the mean of the standard deviation for an area that is generally at the center of the eyebrow. This central area can be a few rows (e.g., 5) above and below the center row of the eyebrow and a few columns (e.g., 5) to the left and right of the center column of the cropped image (or of the column of the eyebrow center point determined at 763 above).

At 767, the right endpoint of the right eyebrow (e.g., FIG. 9B, point 14) is searched for by scanning column-wise the moving average image (from 765) pixel-by-pixel, from its right edge towards its center. At 768, if the intensity of the current pixel in the scan is less than the mean of the skin tone (from 764), and if at 769 the corresponding pixel intensity in the standard deviation image (from 765) is greater than the mean of the standard deviation of the eyebrow (from 766), the pixel is deemed to be the right endpoint of the eyebrow (e.g., point 14 in FIG. 9B). The left endpoint of the right eyebrow (e.g., FIG. 9B, point 16) is determined by scanning the moving average image from the left edge towards the center using the same procedure.

At 770, if either of the eyebrow endpoints as determined above is too close to a border of the cropped eyebrow image, a procedure to refine the above-determined locations is carried out. In an exemplary embodiment, a window (e.g., 10×10 pixels for a 220 PPI resolution image) is cropped around each point and subjected to a mean thresholding operation. The point is then redetected using the same techniques as described above. The eyebrow endpoints are thus refined further to yield a closer binding with the eyebrow ends.

At 771, the eyebrow center point and endpoints are returned.

Referring again to FIG. 7B, at 729, the above procedure is repeated for the center point and endpoints of the left eyebrow. In the illustrative image of FIG. 9B, these are points 1, 2 and 3.

Operation then proceeds to determine the endpoints of the nose.

At 730, a window is cropped based on the center of the nose, determined above. The cropping window size can be determined, for example, in accordance with population statistics for the width and height of the nose and the resolution of the image. At 731, the region growing algorithm described above with reference to FIG. 7D is used to find the points on either side of the nasolabial fold near the nose (e.g., points 7 and 10 in FIG. 9B.)

Similarly, at 732, a suitably sized window is cropped around the center of the lips, determined above. The cropping window size is preferably calculated based on population measures for lip width and height and the image resolution.

At 733, a region growing procedure, similar to that described above for the eyes, is carried out to determine the endpoints of the lips. The detected endpoints of the lips in the illustrative image of FIG. 9B are marked as points 8 and 9.

At 734, the various points determined as described above are validated based on geometric metrics, such as Euclidian distance from one another, from the center of the image, and/or from endpoints on the face (i.e., projections of the feature points on the closest ends of the face). Points that fail the geometric test are re-estimated at 735 by relaxing the thresholds and/or by increasing or decreasing the cropping area size, depending on the context, and re-evaluated at 734. Validated points are output at 736 as feature points for the frontal face image.

A process for detecting facial feature landmark points in an oblique face image will now be described with reference to FIGS. 8A and 8B. For an oblique face image, such as in FIG. 9C, features and their associated points are determined for the near eye (i.e., the eye on the side facing the camera), the visible side of the nose and nasolabial fold, and the near side of the lips. A similar approach such as that described above for the front face image is followed for oblique face images, with some modification.

Figure 8A:
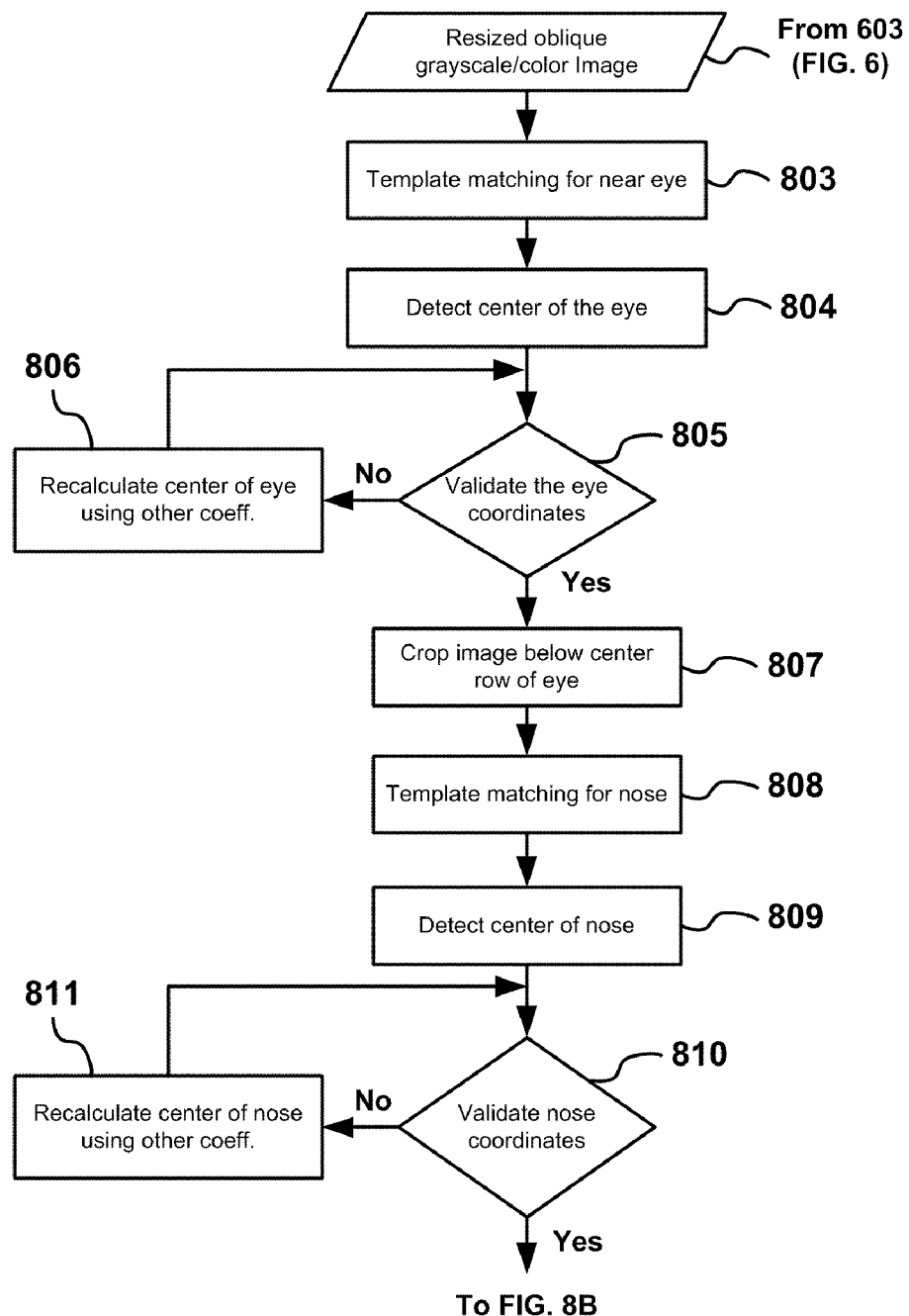
FIGS. 8A and 8B show a high-level flowchart of an exemplary method of detecting a set of facial feature points for an oblique-view facial image, in accordance with the present invention.
Figure 8B:
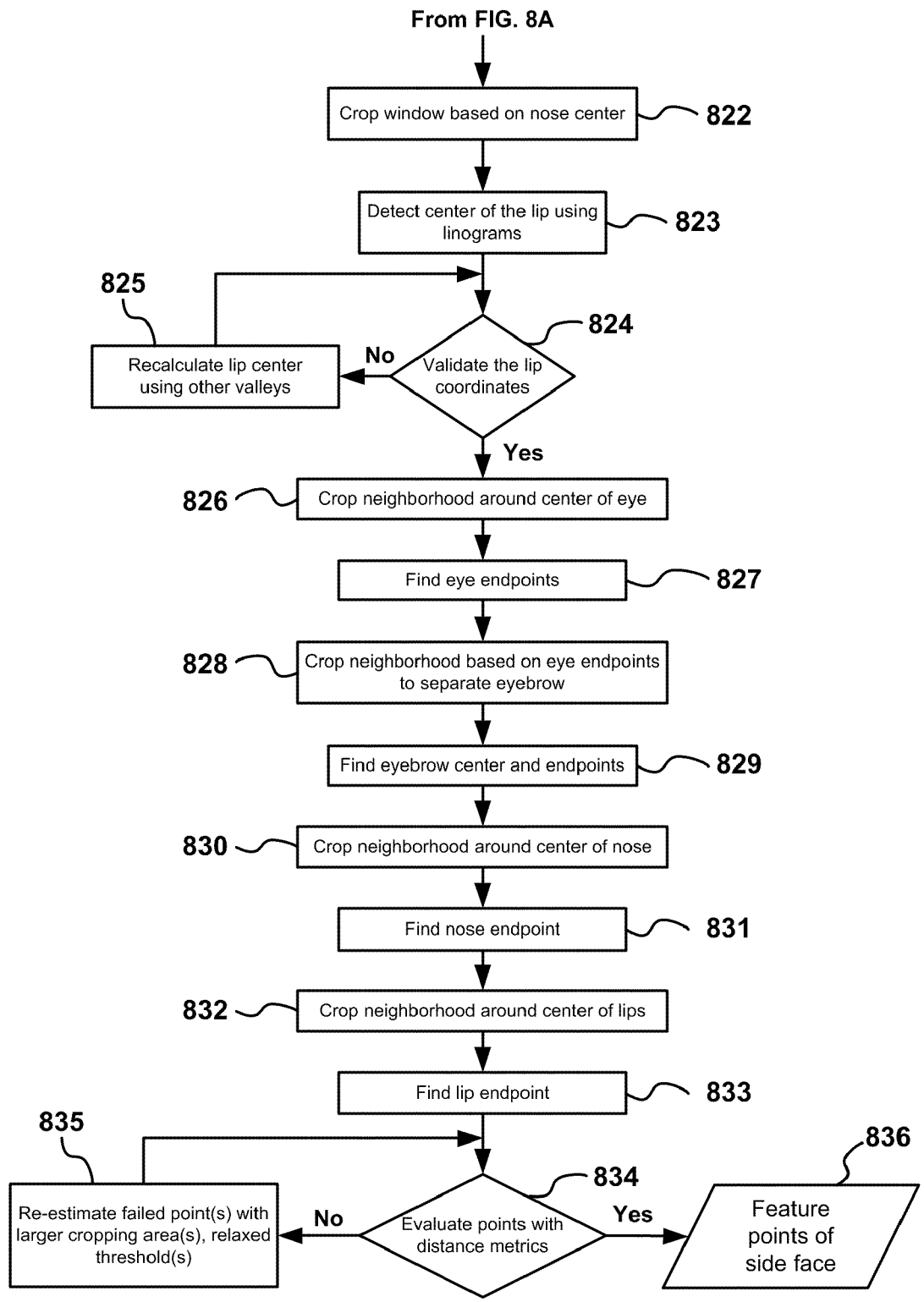

The procedure of FIGS. 8A and 8B uses the resized, grayscale or standard color space image generated in the procedure of FIG. 6, at 603. At 803 and 804, the center of the near eye is determined using a template matching technique. An orientation-specific template for the near eye is selected at 803 using a procedure such as described above with reference to FIG. 7C. The coordinates of the center of the eye are validated at 805 and 806 using a similar procedure as described above for the front-face image.

After the center of the near eye has been detected and validated, as described, the center of the nose is detected next, starting with 807. At 807, the search area for the nose is preferably limited—thereby reducing computational complexity—to rows below the center of the eye. The nose search area is also preferably limited to the columns left of the center of the right eye, for a left facing image (such as that of FIG. 9C), and to the columns right of the center of the left eye, for a right facing image.

At 808, template matching is performed on the nose search area determined in 807. The template matching technique used can be the same as that described above with reference to FIG. 7C. At 809, the location of the point of maximum correlation between the template and the search area is deemed to be the center point of the nose.

Using an iterative procedure at 810 and 811, the coordinates of the center of the nose as detected at 809 are validated using a statistical model similar to that described above for front-view face images. The region below the tip of the nose has a larger gradient strength compared to the skin or the lips. The variation in gradient strength is used as a measure to validate the nose center point at 810. A combined gradient image is obtained by applying horizontal and vertical gradient mask filters to the cropped nose image. If the mean gradient strength of a small window selected below the nose center point (see, e.g., FIG. 15) is above a predetermined threshold, the point is confirmed to be the nose center point. An appropriate value for the threshold can be determined empirically, for example, using multiple facial images, preferably for different skin types. If, however, the mean gradient strength of the small window is not above the predetermined threshold, the center point of the nose is recalculated at 811 using the next highest correlation coefficient until the condition is satisfied at 810.

The centers of various features for an illustrative left-view face image are shown in FIG. 9C. If need be, since the anatomical center of a facial feature will tend to appear offset from the geometric center of the feature as it appears in an oblique-view image, the location of a center point can be adjusted by moving the respective cropping window in the opposite direction.

Once the centers of the facial features of interest have been detected (e.g., eye, eyebrow, nose and lips), as described above, the visible endpoints of the features are then detected. It should be noted that while both endpoints of the near eye and eyebrow will be visible in the oblique view image, only the near endpoints of the nose and lips will be visible. See, e.g., FIG. 9D.

At 826, a local neighborhood region is cropped around the center of the near eye. For a given resolution, the size of this region can be based on measurements for the width and height of the eye for the general population or for a population category relevant to the subject. Operation then proceeds to 827 in which a region growing procedure is carried out to find the endpoints of the eye (e.g., FIG. 9D, points 4 and 6). This procedure is similar to that described above with reference to FIG. 7D.

As in the case of the front face image, in addition to the eye endpoints, it may also be desirable to determine an additional point along the bottom of the eye (e.g., FIG. 9D, point 5) to better delineate the ultimate skin mask contour. A suitable location for this point is at the intersection of the column of the eye center and the bottom row of the eye. The bottom row of the eye can be found by searching in the thresholded cropped image of the eye for the highest row with all non-zero pixels below the lower of the rows of the eye endpoints (e.g., points 4 and 6). Alternatively, instead of locating this point and using it in the mask design, the generally arc-shaped curve between the eye endpoints can be estimated by a suitable curve fitting procedure.

Once the endpoints of the eye have been found at 827, the corresponding eyebrow is processed next, starting with 828. At 828, the eyebrow is isolated by cropping out a region surrounding the eyebrow. The endpoints of the eye (points 4 and 6 in FIG. 9D) and the expected distance between the center of the eye and the eyebrow are used to crop the region surrounding the eyebrow, as described above. Operation then proceeds to 829 in which the center point and endpoints of the eyebrow are determined (e.g., FIG. 9D, points 1, 2 and 3). This procedure is similar to that described above with reference to FIG. 7E.

The nose endpoint that is visible, i.e., on the near side of the face, is then detected. At 830, a window is cropped based on the center of the nose. The cropping window size can be determined, for example, in accordance with population statistics for the width and height of the nose and the resolution of the image. At 831, a region growing procedure based on statistical metrics is carried out from the last column to the first to determine the visible endpoint of the nose (e.g., point 7 in FIG. 9D.)

The lip endpoint that is visible, i.e., on the near side of the face, is then detected. At 832, based on the center of the lips, a window is cropped. The cropping window size can be determined in accordance with general or selected population statistics for the width and height of lips for the resolution of the image. At 833, a region growing procedure is run from the right edge of the image (for a left facing image, such as that of FIG. 9D) or from the left edge of the image (for a right facing image) to determine the visible endpoint of the lips (e.g., point 8 in FIG. 9D.)

The various points determined above are validated at 834 using geometric distance metrics, such as Euclidian distance from one another, from the center of the image or from other reference points. Points that fail the metric measure are re-estimated at 835 by relaxing thresholds, or increasing or decreasing the cropping area size, depending on the context. The re-estimated points are then re-evaluated at 834. Once validated, the feature points for the oblique-view image are output at 836.

The above illustrated oblique-view facial landmark points are a few examples of all the possible landmark points that can be detected in accordance with the present invention. The methods described above can be applied to the detection of other landmark points (e.g., tip of nose, nose and eye-line intersecting point, etc.) using appropriate templates and validation and region-growing techniques, such as described above.

Automatic Registration of Skin Masks

In computer-aided skin analysis, a skin mask designed for a specific region of interest of a skin site of a subject is often needed to be used for a subsequent image of the same skin site of that subject for the purpose of comparison of analysis results. The mask may also need to be used for images of the same skin site captured in different lighting modalities. Although most image capture systems are designed to minimize the potential movements of the skin site, even a very slight movement may cause a misalignment of the ROIs seen in both images. Therefore, it is highly desirable to accurately register the mask designed for a first or "reference" image of a skin site, to a second or "target" image of the skin site. The alignment of the mask to both images will ensure the comparability of the analysis results.

In order to address misalignments of skin ROIs in computer-aided skin analyses, the present invention discloses two types of ROI registration techniques. The first one is a rigid registration, which assumes that the skin ROI in the target image is a rotated and translated version of the skin ROI in the reference image. This type of transformation is useful for registering ROIs where the reference and target images of the skin site are captured in a controlled manner and the movement of the object or ROI is linear across the image. This transformation will preserve the shape and area of the skin mask.

The second ROI registration technique is an elastic registration, which assumes that the target image of the skin site is a free-form, morphed version of the reference image of the skin site. This method slightly changes the shape and area of the skin mask; however, the registered mask is expected to cover the same skin region covered by the reference mask. This type of transformation is useful for registering skin images where the reference image and the target image are captured in a controlled manner and the movement of the object can be large and non-linear across the region covering the object.

Rigid Registration of the Skin Mask

An exemplary embodiment of a rigid mask registration process will now be described with reference to FIG. 10. The process takes as inputs a reference image 1001R and a target image 1001T of the same skin site along with a skin mask 1003 designed for the reference image. The process returns a skin mask 1013 that is registered to the target image 1001T. The resultant mask 1013 covers the same skin regions in the target image as the mask 1003 covers in the reference image.

The reference image 1001R and the target image 1001T can be sequential captures of the same skin site in the same imaging modality, for example, standard white light, UV light, or cross-polarized light, parallel-polarized light, etc. These images can also be sequential captures of the same skin site in different imaging modalities such as standard light and UV light or IR light, standard light and cross-polarized light or parallel-polarized light, or any combination and order of these or other possible modalities. The images 1001R and 1001T can be captured in any order, with any time difference therebetween and by different systems.

Figure 10:
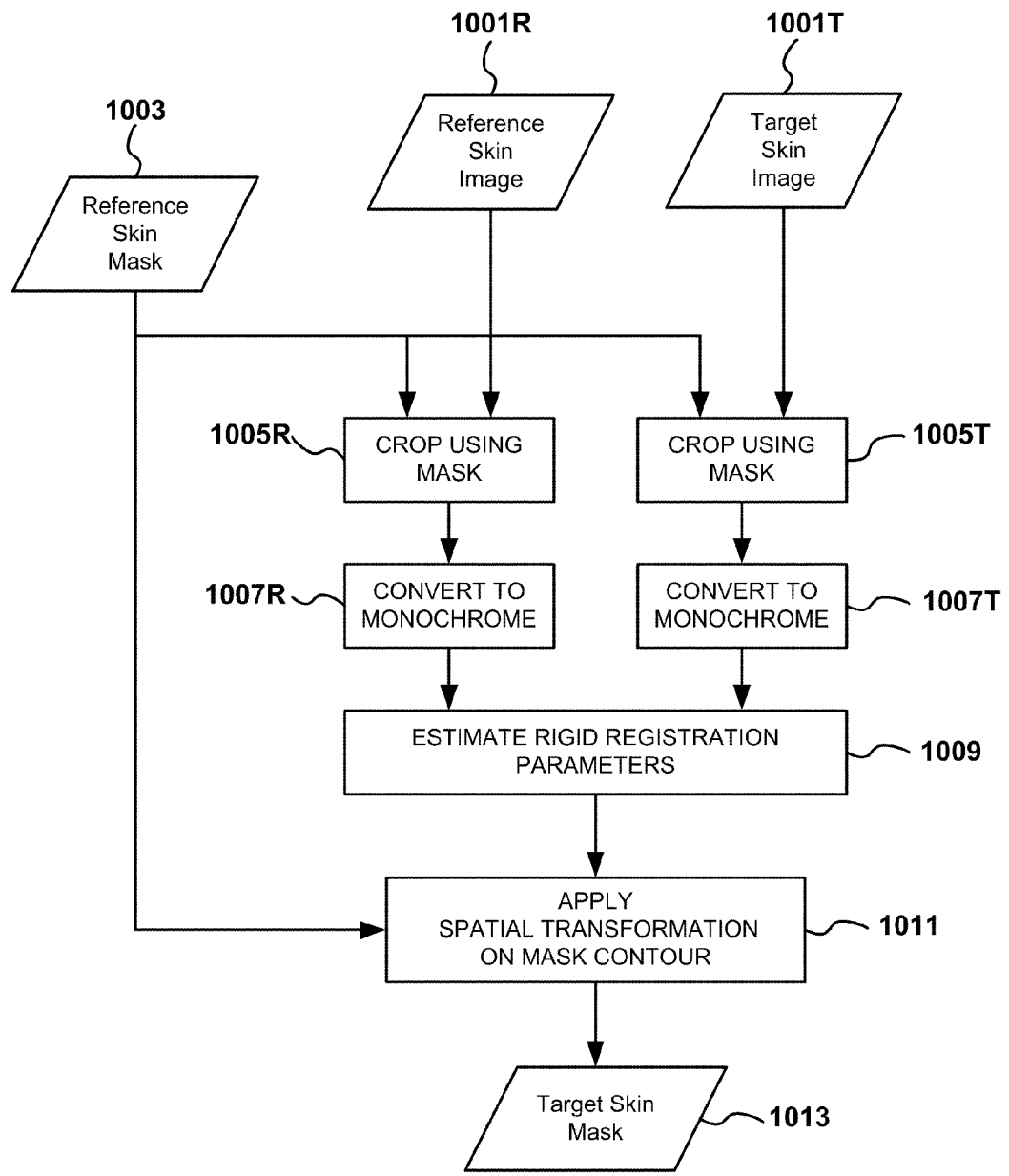
FIG. 10 is a flowchart of an exemplary rigid skin mask registration method for skin site images captured in the same or different imaging modalities, in accordance with the present invention.

As shown in FIG. 10, the reference image 1001R and the target image 1001T are cropped at 1005R and 1005T, respectively, using the reference mask 1003. The cropped portions of the reference and target images are then processed at 1007R and 1007T, respectively, to obtain monochrome images.

Figure 11:
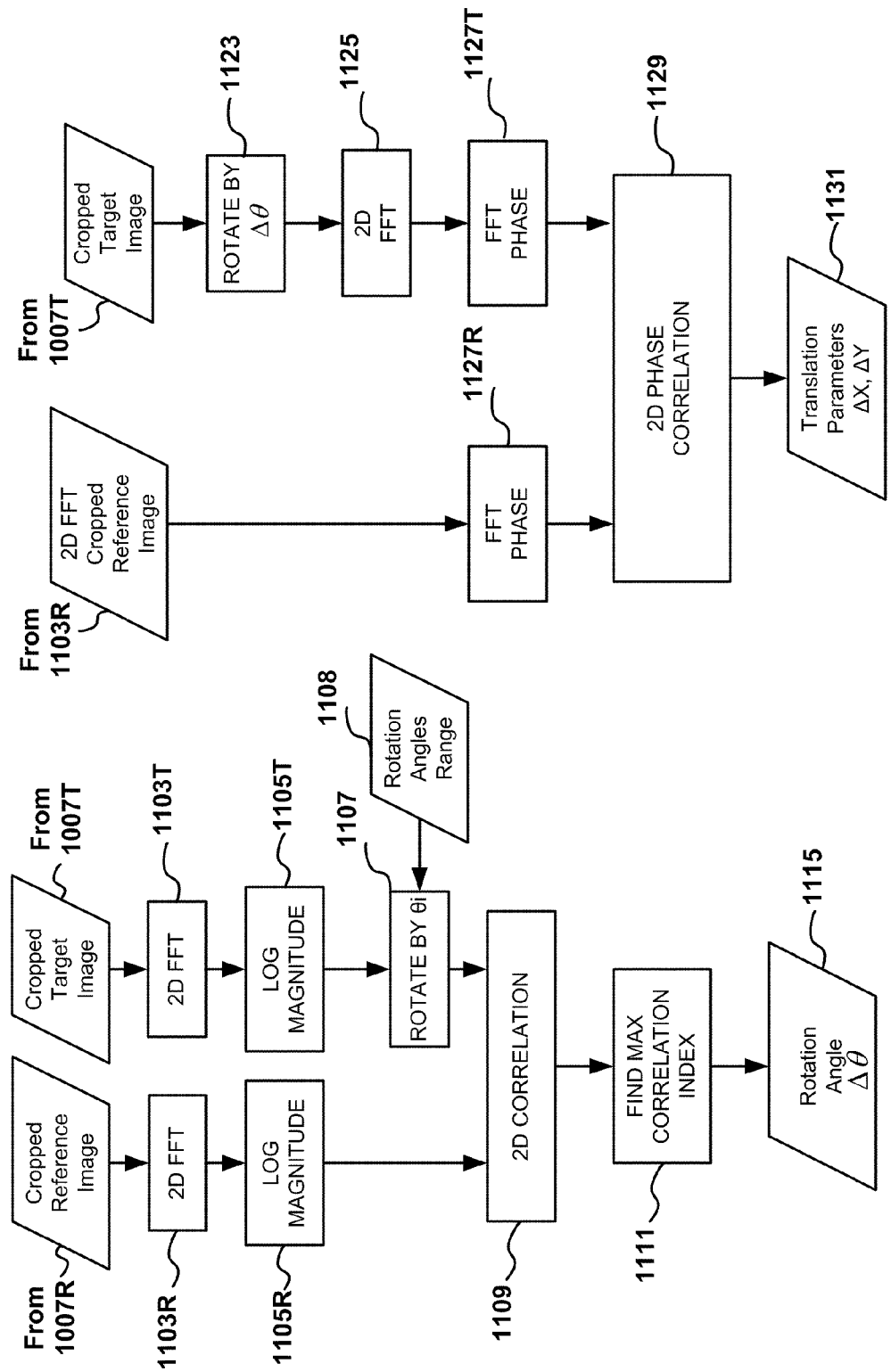
FIG. 11A is a flowchart of an exemplary rotation estimation method and FIG. 11B is a high-level flowchart of an exemplary translation estimation method, in accordance with the present invention.

At 1009, a set of rigid registration parameters are estimated. An exemplary procedure for estimating rigid registration parameters is described below in greater detail with reference to FIG. 11.

Once the rigid registration parameters have been determined, the reference mask 1003 is subjected to a spatial transformation at 1011 to achieve the registered mask 1013 for the target image.

Optionally, a mask registration arrangement in accordance with the present invention can provide a user with the ability, via a graphical user interface or the like, to correct the reference skin mask 1003 and/or the resultant skin mask 1013 by displaying the mask superimposed on the image to which it is registered and allowing the user to manipulate the mask or points thereof.

In the following, the estimation of rigid registration parameters will be described in greater detail.

Estimation of Rigid Registration Parameters

Rigid spatial transformation can be represented by three consecutive spatial transformations: rotation, translation, and scaling. For images captured with the same resolution camera, at the same zoom factor and at the same distance, scaling will usually not be required to register the object of interest in the first image (i.e., the ROI delineated by the skin mask) to the second image. Thus for most cases, the application of a rigid spatial transformation will rotate and translate the ROI (or mask 1003) to register it to the target image (1001T). The rotation ($\Delta\theta$) and translation ($\Delta X$, $\Delta Y$) parameters can be computed given two images containing the object of interest. A computationally efficient technique to compute the rotation and translation parameters utilizing a reference and a target image containing the same object of interest is described in Reddy, et al. "An FFT based technique for translation, rotation and scale invariant image registration", IEEE Transactions on Image Processing, Vol. 5, No. 8, August 1996 (hereinafter the Reddy reference). The rotation and translation transformations can be separated in the magnitudes and phases of Fourier transformed images.

FIG. 11A is a flowchart of an exemplary method of determining the rotation parameter in a rigid spatial transformation such as that used in the method of FIG. 10. The cropped reference and target images (from FIG. 10, 1005R and 1005T or the monochrome versions thereof from 1007R and 1007T) are Fourier transformed using Fast Fourier Transform (FFT) at 1103R and 1103T, respectively. A log operation is then performed on each of the magnitude spectrums at 1105R and 1105T, respectively, to de-emphasize the lower frequency components in the presence of high-frequency components.

The log-magnitude spectrum of the target image from 1105T is a rotated version of the log-magnitude spectrum of the reference image from 1105R. Therefore, the rotation angle can be determined using these two spectrums. In a preferred embodiment, in order to find the best rotation angle $\Delta\theta$, the log-magnitude of the target spectrum is rotated at 1107 by a specific rotation angle $\Delta_i$ chosen from a set of discrete rotation angles 1108. At 1109, the correlation coefficient between the log-magnitude of the reference spectrum and rotated log-magnitude of the target spectrum is determined for that particular rotation angle. 1107 and 1109 are repeated for all possible rotation angles 1108, thereby providing a correlation coefficient for each possible rotation angle. At 1111, the rotation angle that provides the highest correlation coefficient is said to be the best rotation angle 1115.

The above-described technique is efficient for determining small rotation angles, as is typically the case where the reference and target images are captured in a controlled image capture system. For example, the range of [−5 5] degrees in steps of 0.25 degree is adequate for close-booth capture systems such as VISIA. For open capture systems this range can be relaxed, for example to a range of [−10 10] degrees.

Note that the rotation angle can be computed by converting the log-magnitude images from Cartesian coordinates to polar coordinates as described in the Reddy reference. In polar coordinates, the rotation angle is perceived as a displacement in the angle axis. This displacement can be computed using a phase-correlation technique, as described below. This technique, however, is not as effective as the preferred embodiment for small angles, and for images captured in different modalities.

Once the rotation parameter has been determined, as described above, the translation parameters are estimated using a method such as that depicted in FIG. 11B in which the translation parameters are estimated in the phase domain using 2D phase correlation after the correction of the target image for the estimated rotation angle.

As shown in FIG. 11B, the monochrome version of the cropped target image (from FIG. 10, 1007T) is rotated at 1123 by the rotation parameter $\Delta\theta$ determined above. This rotated image is then subjected to a 2D fast-Fourier transform (FFT) at 1125 and an FFT phase operation at 1127T. The FFT phase operation at 1127T determines the phase value for each pixel from the complex values of the FFT image, thereby generating a phase image. Similarly, the transformed cropped reference image from 1103R of the process of FIG. 11A is subjected to an FFT phase operation at 1127R. A 2D phase correlation is then carried out at 1129 using the results of the operations of 1127R and 1127T to return the translation parameters $\Delta X$, $\Delta Y$ at 1131.

Once the rotation and translation parameters have been determined, as described above, they can then be applied to the coordinates of each point of the first mask (1003), registered to the reference image (1001R), to obtain a mask registered to the target image (1001T). (See above, FIG. 10, 1011.)

Figure 13B:
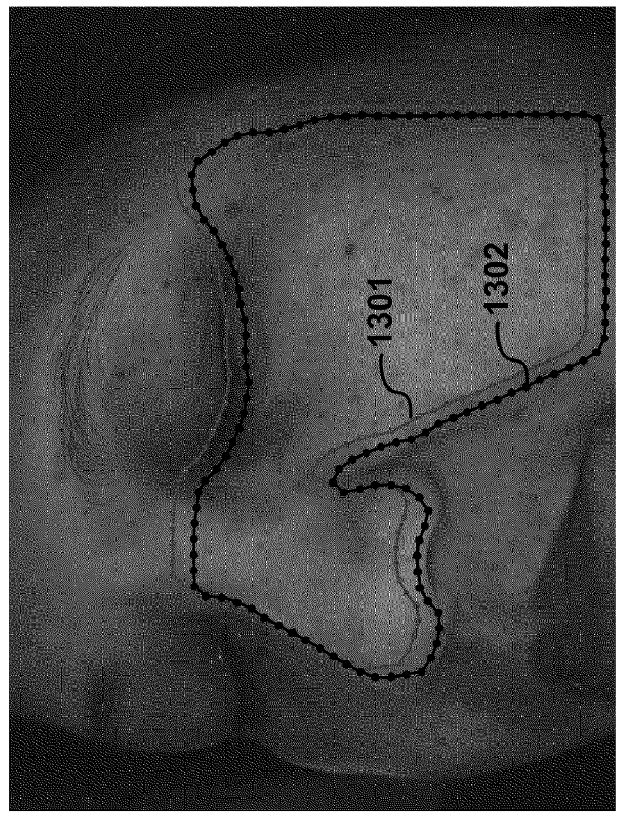
FIGS. 13A through 13F show illustrative facial images captured in different imaging modalities and masks registered for these images, in accordance with the present invention.
Figure 13A:
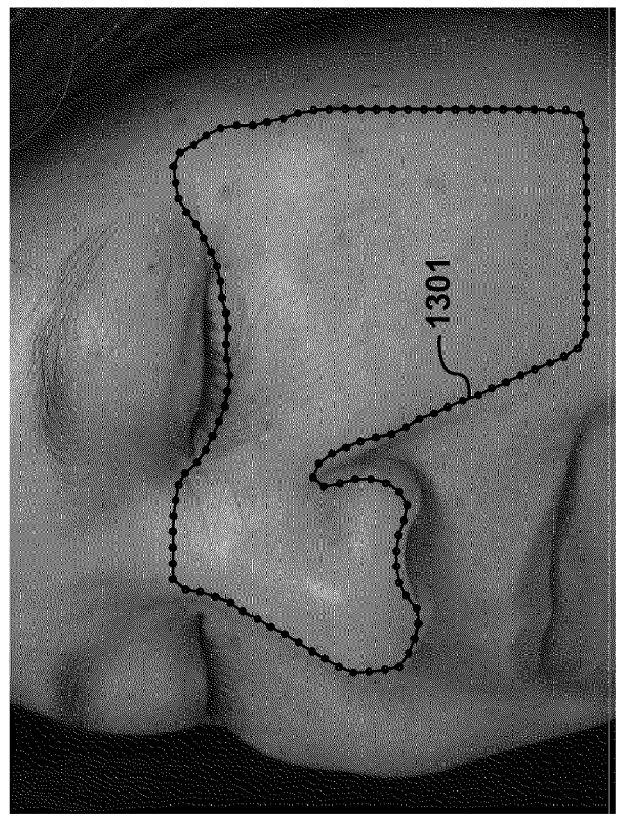

FIG. 13A shows an oblique-view image captured under standard light with a mask contour 1301 of the cheek region superimposed thereon. FIG. 13B shows an oblique view image of the same site captured under UV fluorescence illumination with a slight misalignment. FIG. 13B also shows the original mask contour 1301 and a new mask contour 1302 based thereon which has been registered to the UV fluorescence image. A comparison of the two contours reveals the misalignment between the images and demonstrates the need for registering the mask generated for the first image (FIG. 13A) to the second image (FIG. 13B). The shape and area under the two masks are the same and they cover the same regions of the face.

Figure 13D:
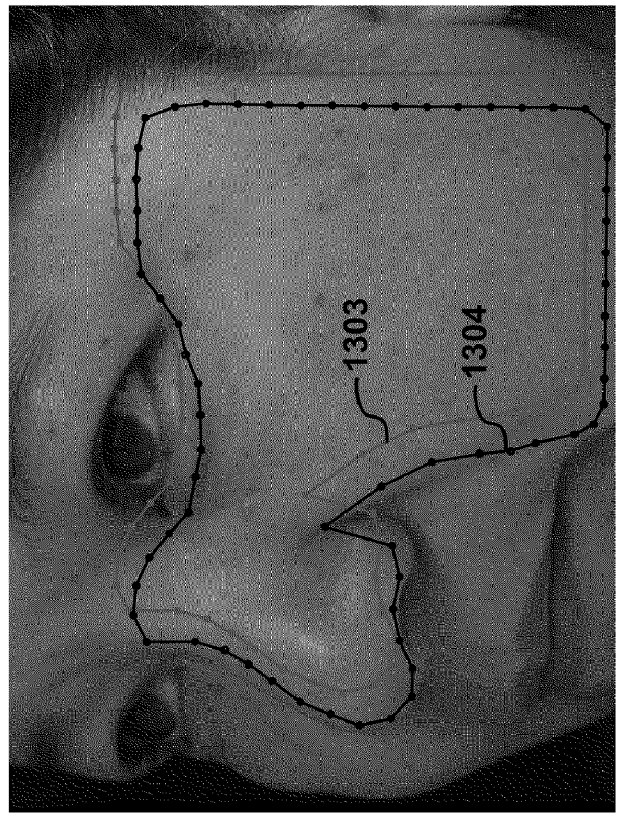
Figure 13C:
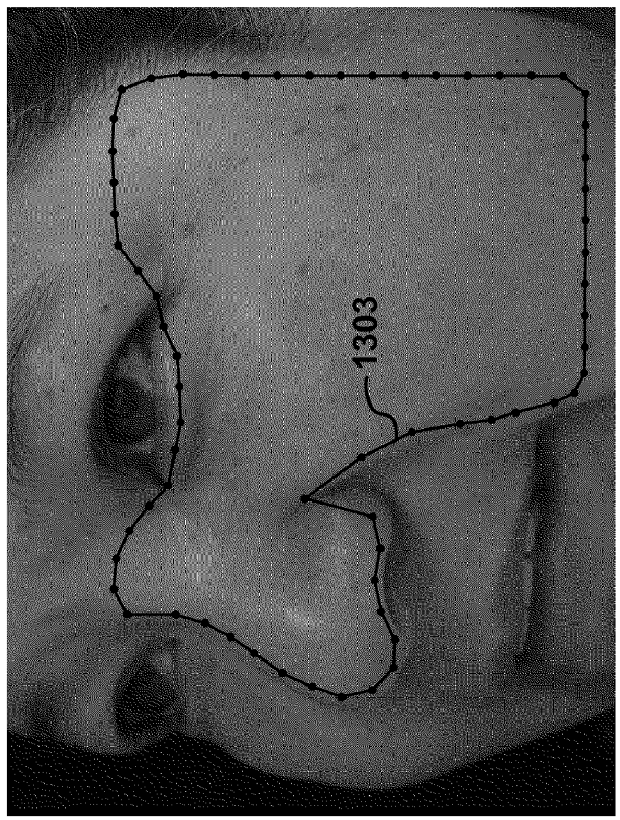

FIG. 13C shows an illustrative oblique-view image captured under standard light with a mask contour 1303 of the cheek region superimposed thereon. FIG. 13D shows a further image of the same site with the original mask contour 1303 and a new mask contour 1304 generated by registering the original mask contour to the image of FIG. 13D using the techniques described above. A comparison of the two contours reveals the misalignment between the images and demonstrates the need for registering the mask generated for the first image (FIG. 13C) to the second image (FIG. 13D). The shape and area under the two masks are the same and they cover the same regions of the face.

Elastic Registration of the Skin Mask

The rigid mask registration technique described above is useful for image capture sequences where the shape of the ROI does not change but only its pose in the image changes. For more complex image capture procedures, however, the shape of the ROI may also change. For example, the skin ROI for face images may change from one image capture to another due to a change in facial expression, muscle movements, etc. The ROI may deform freely in any direction. For these cases, elastic registration is more appropriate to model the morphing of the ROI. Elastic registration relies on finding a set of corresponding points in the reference and target images. Because of this reliance, special care is needed for elastic registration of images captured in different imaging modalities.

Figure 12:
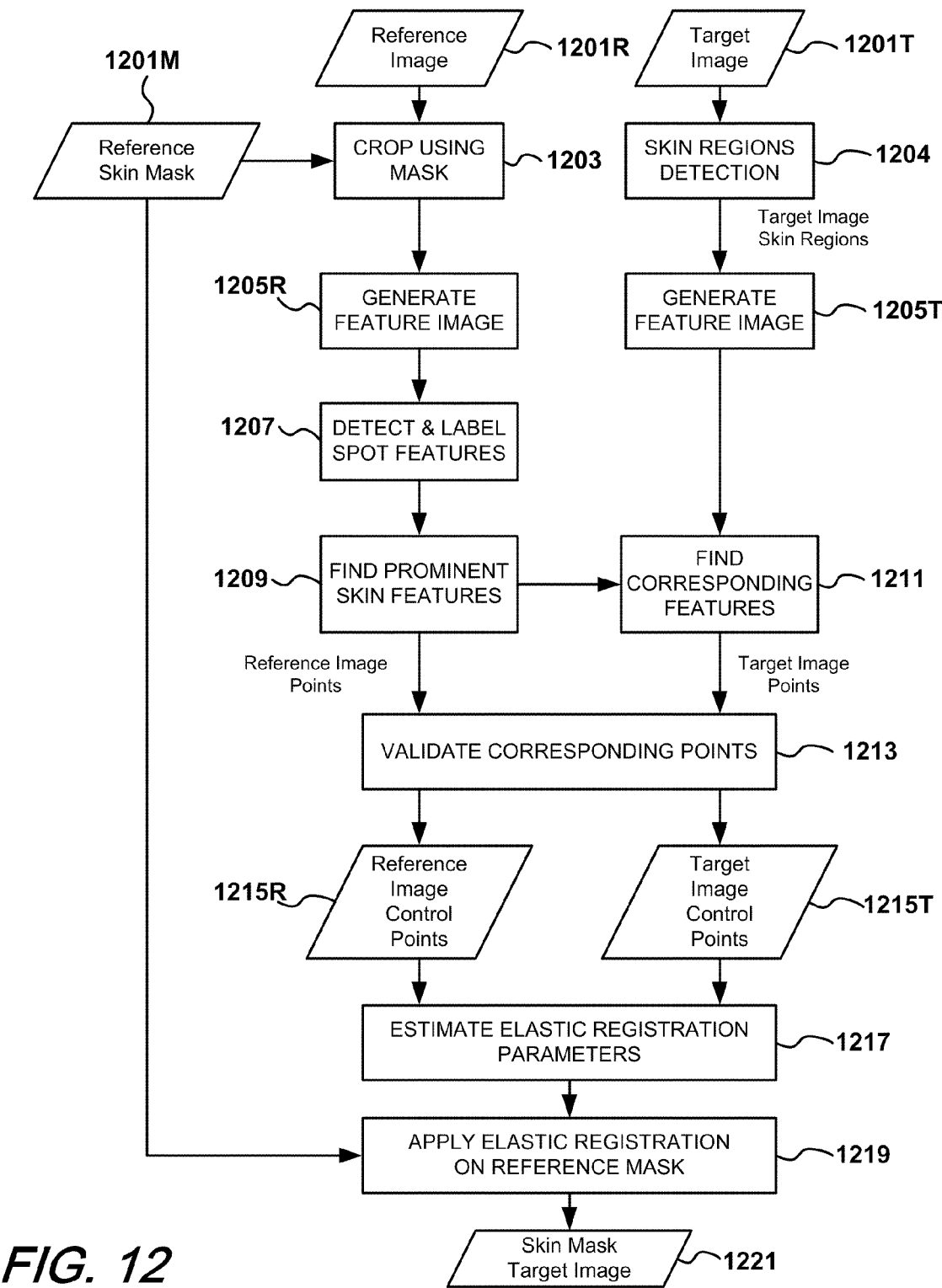
FIG. 12 is a flowchart of an exemplary elastic registration method, in accordance with the present invention.

FIG. 12 is a flowchart of an exemplary elastic registration process between a reference image and a target image which contains a morphed version of a skin ROI that has been delineated in the reference image. There are a variety of known elastic registration techniques (e.g., thin-plate splines (TPS), multi-quadratic (MQ), piecewise linear (PL)), some of which are included as part of image processing software packages. A preferred embodiment of the present invention uses a TPS technique commonly used in biomedical image registration and is more appropriate for defining a smooth mapping between two images with a high degree of elasticity.

The method illustrated in FIG. 12 utilizes a set of corresponding skin features (e.g., spots, pores, porphyrins, etc.) that exist in both the reference and target images and defines a smooth elastic spatial mapping between the two images based upon the coordinates of the corresponding feature pairs. This elastic mapping is then applied to the skin mask given for the reference image to obtain a corresponding skin mask that is registered to the target image. Typically, at least four feature points/pairs will be required to carry out elastic registration.

As shown in FIG. 12, the reference image 1201R is cropped at 1203 using the mask 1201M registered to the reference image. At 1204, a skin region detection procedure is carried out on the target image 1201T to detect the skin regions therein for further processing. The skin regions of the target image can be determined utilizing a skin region detection method such as described above or any other skin detection method suitable for this purpose.

The next step, at 1205R and 1205T, is to generate, from the above images, feature images that are useful for finding a set of corresponding points. Feature images emphasize skin features and are more useful for correspondent feature matching than the original images. In a preferred embodiment of the present invention, the feature image is the average of the blue and green channels of the standard RGB image for standard light or cross-polarized light images. Blue and green channels are known to display hyperpigmented spots and pores better because such features exhibit more absorption in the blue and green spectrums. One can also use other techniques for generating a feature image useful for registration, e.g., the intensity image, or the luminacity (L) channel of the CIE L*a*b* transformed image, or a contrast image using other known contrast generation techniques. For images captured in another imaging modality, the skin features known to appear in that lighting modality can be used for correspondent feature matching. For example, in UV fluorescence imaging, the UV spots or porphyrins can be used as reference features for registration.

Upon generation of the reference and target feature images, skin features (e.g., spots, large pores, wrinkles, hair follicles, etc.) are detected and labeled at 1207 in the reference image. In the exemplary embodiment shown, spot features are used but other features can also be used employing the same approach. Spot features are first detected in the reference image within the region of interest (skin mask) as opposed to being detected first in the skin regions of the target image. It is more efficient and safe to identify spots first in the reference image within the masked area and seek corresponding points in the target image within the skin areas thereof. Note, however, that embodiments in which feature detection is carried out first in the target image or concurrently in both images, are also contemplated by the present invention. U.S. patent application Ser. No. 11/681,509, incorporated herein by reference in its entirety, describes a process for detecting spot features from an intensity or contrast image. Note that only prominent features (e.g., larger than a certain size and above some contrast threshold) are used for correspondence matching because these features are more likely to be detectable in the target image.

After features are detected and labeled, prominent skin features in the reference image are found at 1209. In doing so, the reference image is divided into blocks of a certain size. The block size is preferably based on the desired number of correspondence points. For each block, the most prominent feature is found and enclosed within a bounding patch, which may have a rectangular, circular or other appropriate shape. This bounding patch is used to crop a similarly sized and shaped patch from the reference feature image (from 1205R) and used as a template to search for the same feature in the target feature image (from 1205T). At 1211, a template matching technique is used to find in the target feature image the location of the rectangular patch corresponding to the aforementioned bounding patch from the reference feature image. In a preferred embodiment, the template matching technique uses a normalized cross-correlation measure to find the location of the matching feature, although other metrics (e.g., mutual information (MI), energy of histogram differences (EHD), etc.) can also be used for this purpose. Some matches can be rejected if the matching metric is below a certain threshold. For example, a threshold of 0.5 is used for normalized cross-correlation to reject weak correspondences. This process is repeated for each patch in the reference image and a set of corresponding reference image points and target image points, are generated from 1209 and 1211, respectively.

In finding correspondent points, one can also utilize other anatomical features that are available in the skin image and/or within the neighborhood of the skin ROI. For face images, these features may include, for example, the corners of the eyes, the corners of the lips, and the corners of the nose. Furthermore, the correspondent points obtained from these anatomical features can be combined with skin-feature-based correspondent points. The rule of thumb is to find an adequate number of matching features so that the elastic morphing of the skin ROI can be accurately represented across the entire skin ROI.

At 1213, a procedure is carried out to validate the corresponding points from 1209 and 1211. There are a variety of validation procedures that use geometric techniques, such as Delaunay triangularization, for example, to eliminate pairs that are wrongfully matched. In an exemplary embodiment, triangle geometry is used for three corresponding points, and a triangle similarity measure based on the angles and lengths of the triangle is used to reject outliers. Triangle geometry can also be used to predict the approximate location of a target point based on two matching target points already found and the triangle formed by the three corresponding reference points. Such a process reduces the search space, improves correspondence matching, and reduces processing time.

After the validation of corresponding feature points and the elimination of outliers, one obtains a set of reference image control points 1215R and a corresponding set of target image control points 1215T. Based on these corresponding points, elastic registration (i.e., non-linear spatial transformation) techniques can be used to define a one-to-one spatial mapping between the two images.

At 1217, elastic spatial mapping parameters are estimated based upon the validated matching points. A method of estimating TPS registration parameters from a set of corresponding points that can be used for this purpose is described in Bookstein, et al., "Principal Warps: Thin-Plate Splines and the Decomposition of Deformations", IEEE Transactions on Pattern Analysis and Machine Intelligence, Vol. 11, No. 6, June 1989.

Once the spatial mapping is established at 1217, it is applied to the reference skin mask contour at 1219 to obtain a corresponding skin mask contour 1221 for the target image.

Optionally, a mask registration arrangement in accordance with the present invention can provide a user with the ability, via a graphical user interface or the like, to correct the reference skin mask 1201M and/or the resultant skin mask 1221 by displaying the mask superimposed on the image to which it is registered and allowing the user to manipulate the mask or points thereof.

Figure 13F:
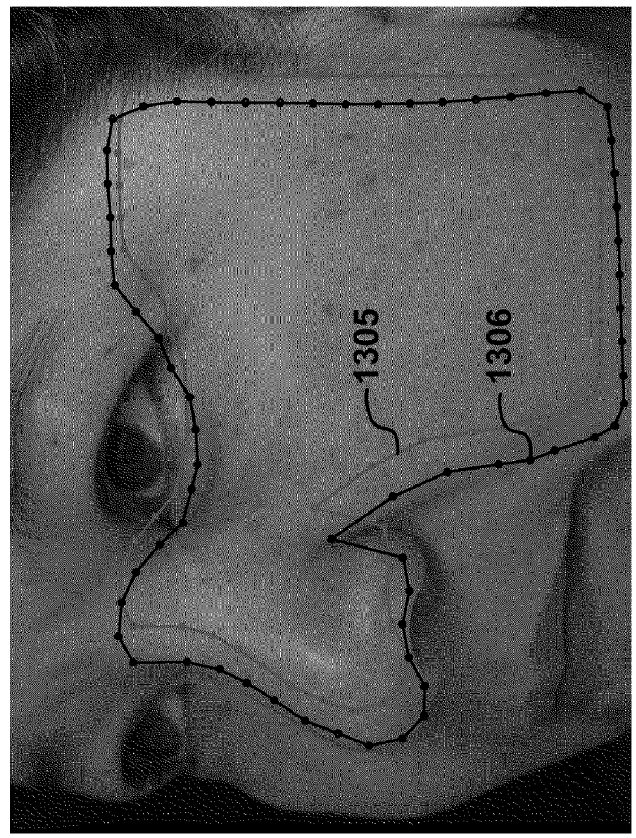
Figure 13E:
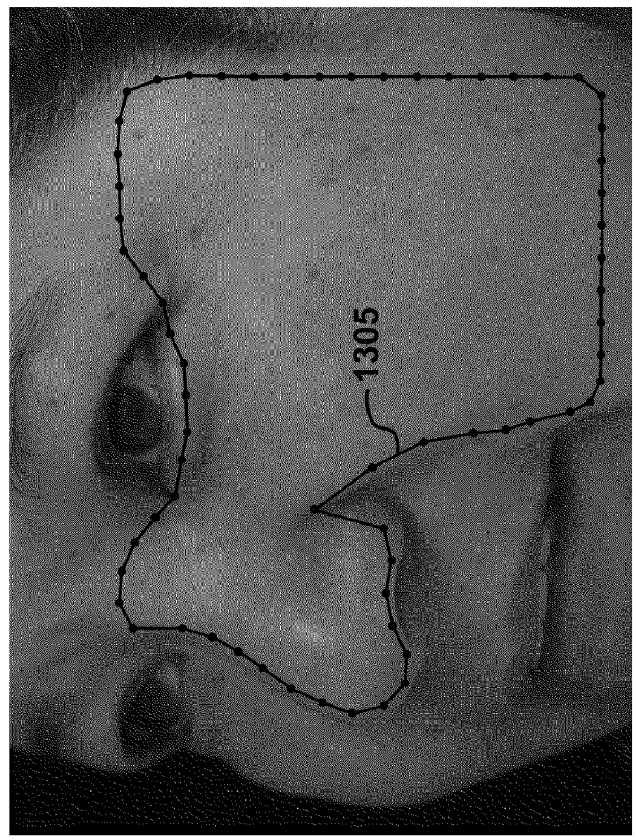

FIG. 13E shows a first oblique-view standard light image with a skin mask contour 1305 of the cheek region generated for the image. FIG. 13F shows a second oblique-view standard light image with the original skin mask contour 1305 and a new skin mask contour 1306 registered to the second image using the elastic registration process described above. A comparison of the two masks reveals that elastic registration has changed the shape of the mask in accordance with the morphing of the cheek region. One can observe that the two masks cover the same skin regions of the face in the images to which they are registered.

One can appreciate the difference between the elastic registration and rigid registration by comparing the registered masks in FIG. 13D (mask 1304) and FIG. 13F (mask 1306). The shape of the mask is preserved in FIG. 13D using rigid registration, however the registered mask 1304 does not entirely cover the same skin regions as the reference mask 1303. The shape of the mask is changed in FIG. 13F using elastic registration, but the registered mask 1306 covers the same skin regions as the reference mask 1305 in the reference image (see FIGS. 13E and 13F).

The present invention can be implemented, for example, using a computer programmed in accordance with the methods described herein. An exemplary hardware configuration that can be used for the present invention is described in U.S. patent application Ser. No. 11/681,509.

It is understood that the above-described embodiments are illustrative of only a few of the possible specific embodiments which can represent applications of the invention. It will be appreciated that while certain techniques and arrangements such as those described above for facial feature and skin detection, for example, may be described in the context of skin mask design, such techniques and arrangements may be applied independently of skin mask design to other applications. Numerous and varied other arrangements can be made by those skilled in the art without departing from the spirit and scope of the invention.

What is claimed is:

1. A method for generating a skin mask delineating a region of interest (ROI) in a skin image comprising:
   detecting skin in the skin image to generate a skin map, wherein detecting skin includes:
       performing a crude skin segmentation operation on the skin image;
       converting the crude skin segmented skin image into a color space image having at least three channels; and
       filtering two of the at least three channels;
       generating a melanin index image from the filtered channels; and
       performing a thresholding operation on the melanin index image to separate skin and non-skin areas in the skin image;
   providing an initial contour based on the skin map; and
   optimizing the initial contour to generate a contour of the skin mask, wherein the skin map and the skin mask each include at least one natural skin boundary.

2. The method of claim 1, wherein the thresholding operation includes determining a threshold based on a histogram of the melanin index image.

3. The method of claim 1, wherein the thresholding operation includes determining a threshold based on data of a population of a relevant skin type.

4. The method of claim 1, comprising:
   eliminating non-skin areas within the skin map using a morphological operation.

5. The method of claim 1, wherein providing the initial contour includes at least one of automatically generating the initial contour from the skin mask and receiving initial contour information.

6. The method of claim 1, comprising:
   applying boundaries to the skin map, the boundaries being based on at least one of a masking guideline and a reference point.

7. The method of claim 6, wherein the reference point includes at least one of an automatically detected landmark point and a user-provided landmark point.

8. The method of claim 6, comprising:
   generating a contour guiding field based on the skin mask, wherein the contour guiding field is used in optimizing the initial contour.

9. The method of claim 8, wherein optimizing the initial contour includes:
   defining an energy functional with terms including the contour guiding field, contour smoothness and integrity, and uniformity of the ROI; and minimizing the energy functional in order to drive the initial contour to the boundaries of the skin map while keeping the contour smooth and intact.

10. The method of claim 9, comprising displaying the contour progression to the boundaries of the skin map.

11. The method of claim 1, comprising displaying the contour of the skin mask with a set of connected points on the skin image.

12. The method of claim 11, comprising providing a user interface for manipulating the contour of the skin mask.

13. The method of claim 1, comprising dividing the skin mask into sub-regions based on at least one landmark point.

14. The method of claim 1, comprising storing data representing the skin mask in association with the skin image.

15. The method of claim 1, wherein the skin image is a front-view or an oblique-view face image.

16. The method of claim 1, wherein the skin image is a full-face image, an image of a portion of the face, or an image of an anatomical region containing skin.

17. The method of claim 1, wherein the skin image is a Red, Green, Blue (RGB) or L*a*b* color image.

18. The method of claim 1, comprising:
processing the skin map so that it is a contiguous and smooth contour.

19. The method of claim 1, wherein
the crude skin segmented skin image is converted into a L*a*b* color space image;
the filtering is performed on the L* and b* channels of the L*a*b* color space image; and
the melanin index image is generated from the filtered L* and b* channels.

20. The method of claim 1, wherein the skin mask is anatomically standardized.

* * * * *